US011331341B2

(12) United States Patent
Hedrick et al.

(10) Patent No.: US 11,331,341 B2
(45) Date of Patent: May 17, 2022

(54) COMBINATION THERAPIES THAT ENHANCE ANTIMICROBIAL/ANTICANCER ACTIVITIES

(71) Applicants: International Business Machines Corporation, Armonk, NY (US); Agency for Science, Technology and Research, Singapore (SG)

(72) Inventors: James L. Hedrick, Pleasanton, CA (US); Yi Yan Yang, Singapore (SG); Nathaniel H. Park, San Jose, CA (US); Jiayu Leong, Singapore (SG); Chuan Yang, Hillington Green (SG); Xin Ding, Singapore (SG); Yiran Zhen, Singapore (SG); Cherylette Anne Alexander, Singapore (SG); Jye Yng Teo, Singapore (SG)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/832,452

(22) Filed: Mar. 27, 2020

(65) Prior Publication Data
US 2021/0299160 A1 Sep. 30, 2021

(51) Int. Cl.
*A61K 31/785* (2006.01)
(52) U.S. Cl.
CPC ................... *A61K 31/785* (2013.01)

(58) Field of Classification Search
None
See application file for complete search history.

(56) References Cited

U.S. PATENT DOCUMENTS

| 10,463,746 | B2 | 11/2019 | Boday et al. |
| 2014/0235790 | A1 | 8/2014 | Stayton et al. |
| 2017/0303541 | A1* | 10/2017 | Chin ...................... A01N 47/44 |
| 2017/0319704 | A1 | 11/2017 | Chin et al. |
| 2018/0228835 | A1 | 8/2018 | Chin et al. |

OTHER PUBLICATIONS

Chin et al., Macromolecules, 2013, vol. 46, pp. 8797-8807 (Year: 2013).*
Park et al., J. Am. Chem. Soc., 2018, vol. 140, pp. 4244-4252 (Year: 2018).*

(Continued)

*Primary Examiner* — Brian Gulledge
(74) *Attorney, Agent, or Firm* — Amin, Turocy & Watson, LLP

(57) ABSTRACT

Techniques regarding a chemical composition that can be utilized within one or more combination therapies to treat a microbial infection are provided. For example, one or more embodiments described herein can comprise a chemical composition that includes a first triblock polymer comprising a quaternary ammonium functionalized polycarbonate block and exhibiting anticancer activity via a lytic mechanism. The chemical composition can also include a second triblock polymer comprising a guanidinium functionalized polycarbonate block and exhibiting anticancer activity via a translocation mechanism.

11 Claims, 28 Drawing Sheets

(56) References Cited

OTHER PUBLICATIONS

Zhong et al., Biomaterials, 2019, vol. 199, pp. 76-87 (Year: 2019).*
Chin, et al. "A macromolecular approach to eradicate multidrug resistant bacterial infections while mitigating drug resistance onset." Nature Communications; DOI: 10.1038/s41467-018-03325-6; 2018; 14 pages.
Lei, et al. "The antimicrobial peptides and their potential clinical applications." Am J Transl Res 2019;11(7):3919-3931. www.ajtr.org/ISSN:1943-8141/AJTR0095989. 13 pages.
Felicio, et al. "Peptides with Dual Antimicrobial and Anticancer Activities." Frontiers in Chemistry, Feb. 2017, vol. 5, Article 5. 9 pages.
Pan, et al. "Polymeric Co-Delivery Systems in Cancer Treatment: An Overview on Component Drugs' Dosage Ratio Effect." Molecules 2019, 24, 1035; doi:10.3390/molecules24061035. 32 pages.
Park, et al. "Addressing Drug Resistance in Cancer with Macromolecular Chemotherapeutic Agents." J. Am. Chem. Soc. 2018, 140, 12, 4244-4252. 9 pages.
Zhong, et al. "Polymers with distinctive anticancer mechanism that kills MDR cancer cells and inhibits tumor metastasis." Biomaterials, 2019, https://doi.org/10.1016/j.biomaterials.2019.01.036. 43 pages.
"A to Z List of Cancer Drugs" NIH National Cancer Institute, https://www.cancer.gov/about-cancer/treatment/drugs. Last Accessed Mar. 9, 2020. 18 pages.
List of IBM Patents or Applications Treated as Related, Mar. 2020.

* cited by examiner

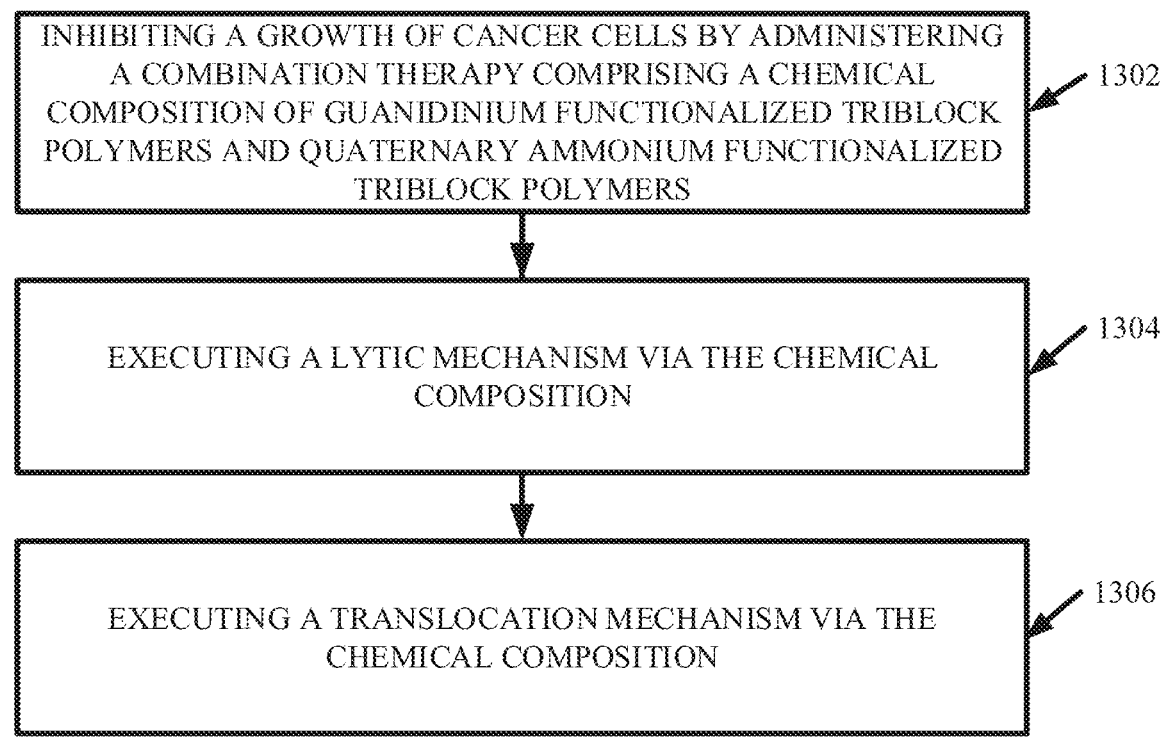

| | MIC (µg/ml) | | | | | | | | | | | |
|---|---|---|---|---|---|---|---|---|---|---|---|---|
| | Gram-Positive | | Gram-Negative | | | | | | | | Fungus | |
| Polymers | S. aureus | | A. baumannii | | E. coli | | K. pneumoniae | | P. aeruginosa | | C. albicans | |
| | MIC | MBC | MIC | MBC | MIC | MBC | MIC | MBC | MIC | MBC | MIC | MBC |
| pQuat_20 | 3.9 | 3.9 | 15.6 | 31.3 | 15.6 | 62.5 | 62.5 | 125 | 125.0 | >1000 | 500-1000 | >1000 |
| pBut_10 | 7.8 | 15.6 | 15.6 | 15.6 | 15.6 | 15.6 | 15.6 | 15.6 | 31.3 | 31.3 | 31.3 | 31.3 |
| pBut_20 | 3.9 | 7.8 | 7.8 | 7.8 | 7.8 | 7.8 | 7.8 | 15.6 | 15.6 | 15.6 | 15.6 | 15.6 |
| a | 7.8 | 7.8 | 7.8 | 7.8 | 7.8 | 15.6 | 15.6 | 15.6 | 31.3 | 31.3 | 62.5 | 62.5 |
| b | 3.9 | 7.8 | 7.8 | 15.6 | 15.6 | 31.3 | 15.6 | 31.3 | 62.5 | 62.5 | 62.5 | 125.0 |

```
┌─────────────────────────────────────────────────┐
│ INHIBITING A GROWTH OF CANCER CELLS BY ADMINISTERING │ ← 2602
│        A COMBINATION THERAPY COMPRISING A        │
│   CHEMOTHERAPEUTIC AGENT AND AN ANTIMICROBIAL    │
│                     POLYMER                      │
└─────────────────────────────────────────────────┘
                        │
                        ▼
┌─────────────────────────────────────────────────┐
│       ENHANCING AN ANTICANCER ACTIVITY OF THE    │ ← 2604
│  CHEMOTHERAPEUTIC AGENT BY THE PRESENCE OF THE   │
│              ANTIMICROBIAL POLYMER               │
└─────────────────────────────────────────────────┘
```

COMBINATION THERAPIES THAT ENHANCE ANTIMICROBIAL/ANTICANCER ACTIVITIES

BACKGROUND

The subject disclosure relates to one or more combination therapies that can enhance the antimicrobial and/or anticancer activities of therapeutic agents, and more specifically, to combination therapies utilizing chemical compositions comprising quaternary ammonium functionalized and/or guanidinium functionalized polycarbonate polymers.

Cancer treatment generally involves surgical resection of the tumor followed by chemotherapy or radio-therapy. However, due to the high risks of relapse, metastasis, and/or therapeutic resistance (e.g., either intrinsic or acquired during chemotherapy); cancer treatment often ends with limited success. Additionally, the health care field has experienced an emergence of therapeutic resistance pathogens, such as bacteria with antimicrobial resistance.

Host defense peptides ("HDPs") and synthetic antimicrobial peptides ("AMPs"), designed to eradicate antimicrobial resistant bacteria, have been shown to also have cytotoxicity against cancer cells. These amphiphilic, cationic peptides are capable of interacting with negatively charged membranes such as those found on bacteria. Analogously, the plasma membranes of cancer cells are more negatively charged than their healthy counterparts, owing to a high abundance of anionic constituents including phosphatidylserine, sialic acid, or heparin sulfate. Although oncolytic peptides show potent anticancer activity, high manufacturing costs and instability to proteolysis limit their potential clinical applications.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, chemical compositions and/or methods regarding one or more combination therapies that can enhance the antimicrobial and/or anticancer activities of therapeutic agents are described.

According to an embodiment, a chemical composition is provided. The chemical composition can comprise a first triblock polymer comprising a quaternary ammonium functionalized polycarbonate block and exhibiting anticancer activity via a lytic mechanism. The chemical composition can also comprise a second triblock polymer comprising a guanidinium functionalized polycarbonate block and exhibiting anticancer activity via a translocation mechanism. An advantage of such a chemical composition can be the treatment of cancer with chemical compounds that exhibit low toxicity to healthy cells.

In some examples, the first triblock polymer and the second triblock polymer form a stereocomplex that provides kinetic stability. An advantage of such a chemical composition can be combination therapy compositions that exhibit high kinetic stability.

According to another embodiment, a chemical composition is provided. The chemical composition can comprise a quaternary ammonium functionalized polycarbonate polymer that exhibits antimicrobial activity via a lytic mechanism. The chemical composition can also comprise a guanidinium functionalized polycarbonate polymer that exhibits antimicrobial activity via a translocation mechanism. An advantage of such a chemical composition can be the treatment of therapeutic resistant microbes.

In some examples, the quaternary ammonium functionalized polycarbonate polymer and the guanidinium functionalized polycarbonate polymer can be cationic and biodegradable. An advantage of such a chemical composition can be a low toxicity to human patients.

According to another embodiment, a chemical composition is provided. The chemical composition can comprise a chemotherapeutic agent and a macromolecular chemotherapeutic polycarbonate polymer. The macromolecular chemotherapeutic polycarbonate can comprise a functional group selected from the group consisting of a quaternary ammonium functional group and a guanidinium functional group. An advantage of such a chemical composition can be the reduction of minimum inhibitory concentration values of chemotherapeutic agents while mitigating toxicity.

In some examples, the macromolecular chemotherapeutic polycarbonate polymer can enhance an anticancer activity of the chemotherapeutic agent towards a strain of therapeutic-resistant cancer cells. An advantage of such a chemical composition can be the treatment of therapeutic resistant cancer cells.

BRIEF DESCRIPTION OF THE DRAWINGS

FIG. 13 illustrates a flow diagram of an example, non-limiting method that can facilitate performing a combination therapy utilizing one or more quaternary ammonium functionalized polycarbonates and/or guanidinium functionalized polycarbonates to inhibit the growth of cancer cells in accordance with one or more embodiments describe herein.

FIG. 26 illustrates a flow diagram of an example, non-limiting method that can facilitate performing a combination therapy utilizing one or more chemotherapeutic agents and macromolecular chemotherapeutic polycarbonate polymers to inhibit the growth of cancer cells in accordance with one or more embodiments described herein.

DETAILED DESCRIPTION

Figure 1:
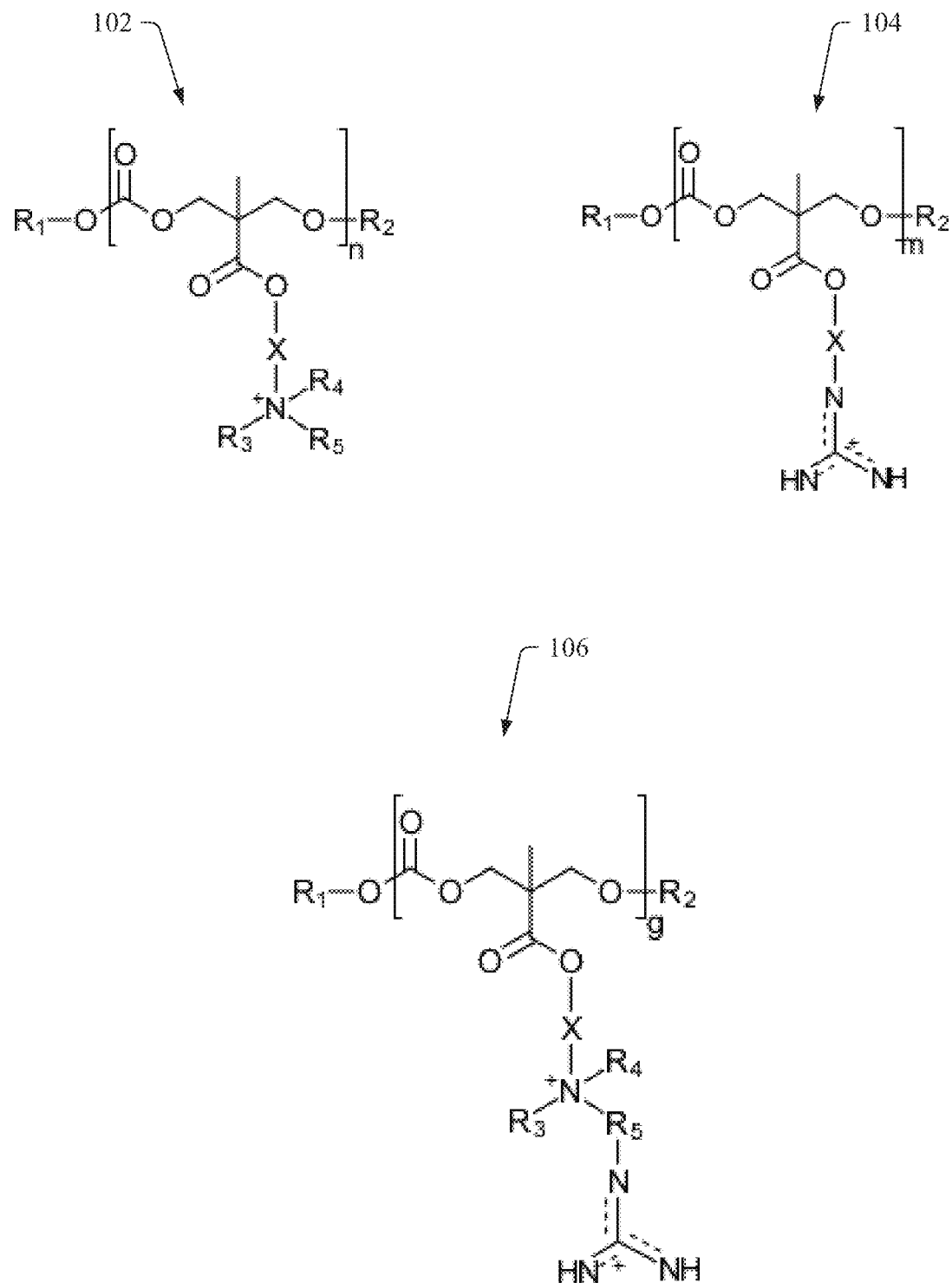
FIG. 1 illustrates a diagram of example, non-limiting chemical structures that can characterize antimicrobial and/or anticancer polymers in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Given the problems with other approaches to inhibiting the growth of cancer cells and/or antimicrobial resistant pathogens; the present disclosure can be implemented to produce a solution to one or more of these problems through combination therapies that can enhance the anticancer and/or antimicrobial activity of one or more therapeutic agents. Advantageously, one or more chemical compositions utilized in the combination therapies described herein can enhance the anticancer activity of one or more biodegradable cationic polymers to inhibit the growth of cancer cells. Also, one or more chemical compositions utilized in the combination therapies described herein can enhance the antimicrobial activity of one or more antimicrobial polymers to inhibit the growth of one or more pathogens, including antimicrobial resistant pathogens. Additionally, one or more chemical compositions utilized in the combination therapies described herein can enhance the anticancer activity of one or more chemotherapeutic agents to inhibit the growth of cancer cells.

Various embodiments described herein can regard chemical compositions and/or combination therapies that can enhance the anticancer and/or antimicrobial activity of one or more quaternary ammonium functionalized polycarbonates, guanidinium functionalized polycarbonates, and/or chemotherapeutic agents. Quaternary ammonium functionalized polycarbonates and guanidinium functionalized polycarbonates can terminate bacteria and/or inhibit bacteria growth based on distinctive mechanisms, membrane disruption and membrane translocation followed by precipitation of cytosolic biomacromolecules, respectively. The combination of these two polymers can achieve additive and synergistic effects against microbe cells (e.g., Gram-positive bacteria, Gram-negative bacteria, and/or fungus) and/or cancer cells. Moreover, the use of either quaternary ammonium functionalized polymers or guanidinium-functionalized polymers can reduce doxorubicin resistance phenotype in doxorubicin resistant cancer cell lines. Further, the combination of quaternary ammonium functionalized polycarbonates and guanidinium functionalized polycarbonates can enhance anticancer activity.

As used herein, the term "combination therapy" can refer to the use of multiple chemical compounds to treat an illness and/or disease. The chemical compounds can comprise pharmaceutical compounds, such as chemotherapeutic agents. Additionally, the chemical compounds can comprise compounds other than pharmaceutical compounds, such as antimicrobial polymers (e.g., functionalized polycarbonates and/or polyionenes). The multiple chemical compounds can be used in combination to achieve one or more synergistic effects, which can enhance and/or facilitate one or more therapeutic treats of the chemical compounds. In addition, the combination can comprise various types of chemical compounds. For example, one or more pharmaceutical compounds can be combined with one or more antimicrobial polymers in one or more combination therapies. Further, treating the illness can comprise: inhibiting the illness, eradicating the illness, delaying the illness, mitigating the illness, reducing the development of a resistance to treatment by the illness, a combination thereof, and/or the like. Moreover, the illness (e.g., an infection) can be caused by one or more microbes (e.g., bacteria, such as Gram-negative bacteria) and/or cancer cells.

As used herein the term, "lytic mechanism" can refer to the destruction of a cell, such as a microbe and/or cancer cell, via membrane disruption. One or more chemical compounds can execute a lytic mechanism via the following steps. First, the chemical compounds can be attracted to the target cell through electrostatic association (e.g., the chemical compound can be cationic, and a membrane of the target cell can be anionic). Next, one or more functional groups of the chemical compounds (e.g., hydrophobic functional groups) can insert themselves into the target cell's bilayer membrane. The membrane insertion can result in disruption of the cell membrane and lysis of the target cell.

As used herein the term "translocation mechanism" can refer to the destruction of a cell, such as a microbe and/or cancer cell, via membrane translocation. One or more chemical compounds can execute a translocation mechanism via the following steps. First, the chemical compounds can be attracted to the target cell through electrostatic association (e.g., the chemical compounds can be cationic, and a membrane of the target cell can be anionic). One or more functional groups of the chemical compounds (e.g., guanidinium functional groups) can form one or more multidentate hydrogen-bonds with one or more phosphate groups in the membrane of the target cell. The one or more multidentate hydrogen-bonds can neutralize a charge of the membrane, and thus can promote membrane translocation. After entering the target cell, the one or more chemical compounds can associate with an inner leaflet of the membrane. Further, the chemical compounds can release from the inner leaflet and interact with one or more cytosolic proteins and/or genes of the cell, thereby precipitating the cytosolic materials (e.g., proteins, enzymes, and/or genes).

Unless otherwise stated, materials utilized to facilitate the experiments, tables, charts, diagrams, and/or the like described herein can be acquired from the following sources. The bacteria *Staphylococcus aureus* ("*S. aureus*") (e.g., strain 6538), *Escherichia coli* ("*E. coli*") (e.g., strain 25922), *Pseudomonas aeruginosa* ("*P. aeruginosa*") (e.g., strain 700603), therapeutic-susceptible *Acinetobacter baumannii* ("*A. baumannii*") (e.g., strain 1709), therapeutic-resistant *A. baumannii* (e.g., strain 1789), *Klebsiella pneumoniae* ("*K. pneumoniae*") (e.g., strain 9027), *Candida albicans* ("*C. albicans*") (e.g., strain 10231) can be acquired from American Type Culture Collection ("ATCC"). Additionally, human lung adenocarcinoma (e.g., strains HCC827 and A549), human breast tumor ("BT474"), therapeutic-susceptible human breast cancer ("MCF7"), therapeutic-resistant human breast cancer ("MCF7/ADR"), human liver carcinoma ("HepG2"), and/or therapeutic resistant ovarian cancer ("SK-OV-3-TR") cell lines can be purchased from ATCC.

Dulbecco's modified eagle medium ("DMEM") and Roswell Park Memorial Institute ("RPMI") 1640 medium containing 25 millimoles (mM) Hepes and L-Glutamine can be used to culture HCC827 and A549 cells, respectively, at 37 degrees Celsius (° C.) in 5% carbon dioxide ($CO_2$). All media can be supplemented with 10% fetal bovine serum ("FBS"), 100 units per milliliter (U/mL) of penicillin and 100 micrograms per milliliter (m/mL) of streptomycin. Further, [4,5-Dimethylthiazol-2-yl]-2,5-diphenyl tetrazolium bromide ("MTT") solution can be prepared by dissolving MTT in phosphate-buffered saline ("PBS", pH 7.4) at 5 milligrams per milliliter (mg/mL), which can be then filtered to remove blue formazan crystals (e.g., using a 0.22 micrometer (μm) filter).

In various embodiments, the various triblock polycarbonate polymers described herein (e.g., functionalized with quaternary ammonium and/or guanidinium) can be dissolved in deionized water at 250 milligrams per liter (mg/L) under vortexing for 10 minutes and left to stand for 1.5 hours at room temperature to promote micellar formation. Additionally, wherein the various triblock polycarbonate polymers described herein (e.g., functionalized with quaternary ammonium and/or guanidinium) can form stereocomplex micelles, the molar ratio of individual polymers can be kept at 1:1.

In various embodiments, the cytotoxicity of the various triblock polycarbonate polymers (e.g., functionalized with quaternary ammonium and/or guanidinium) and/or combination therapies described herein can be examined through one or more 3-(4,5-Dimethylthiazol-2-yl)-2,5-diphenyltetrazolium bromide for ("MTT") assays and depicted via one or more cytotoxicity graphs. For example, target cells can be seeded onto 96 well plates at a density of $1\times10^4$ cells per well and incubated overnight in 100 microliters (μL) of medium at 37° C., 5% $CO_2$. Following 1.5 hours of standing at room temperature, the micellar solutions of the given triblock polycarbonate polymers and/or combination therapies can be then diluted in media to obtain various concentrations from 200 mg/L to 0.78 mg/L. The medium in each well can then replaced with the sample solution at 100 μL and the plates can be incubated 37° C., 5% $CO_2$ for either 24 hours or 48 hours. Five replicates can be tested for each concentration. Medium can be used as the control. At the end of incubation, the sample solution can be replaced with 100 μL of fresh medium and 20 μL of MTT solution (e.g., 5 mg/mL in PBS). The plates can then be maintained at 37° C., 5% $CO_2$ for 3.5 hours. The medium solution can be subsequently removed and 150 μL of dimethyl sulfoxide ("DMSO") can be added to each well to dissolve the purple formazan crystals internalized by live cells. After a gentle agitation for 15 minutes, the absorbance of formazan crystals can be taken to be that at 550 nanometers (nm) subtracted by that at 690 nm using a microplate reader. Cell viability can be expressed as a percentage of absorbance of the control cells.

FIG. 1 illustrates a diagram of example, non-limiting chemical structures that can characterized one or more functionalized polycarbonate polymers that can utilized in one or more combination therapies to enhance antimicrobial and/or anticancer activity in one or more embodiments described herein. Repetitive description of like elements employed in other embodiments described herein is omitted for sake of brevity. FIG. 1 illustrates a quaternary ammonium functionalized polycarbonate structure 102, a guanidinium functionalized polycarbonate structure 104, and/or a quaternary ammonium and guanidinium functionalized polycarbonate structure 106.

In one or more embodiments, the quaternary ammonium functionalized polycarbonate structure 102 can comprise a first functional group (e.g., represented by "$R_1$") and/or a second functional group (e.g., represented by "$R_2$") bonded to a functionalized polycarbonate block. In one or more embodiments (e.g., within one or more combination therapies directed to enhance anticancer activity), the one or more first functional groups can be characterized as a targeting moiety, dye, improved solubility agent, and/or structure-directing agent (e.g., micelle forming group). Further, example structures that can comprise the one or more first functional groups can include, but are not limited to: polyethylene glycol ("PEG"), mannose, galactose, glucose, biotin, folic acid, antibodies, peptide, a combination thereof, and/or the like. In one or more embodiments (e.g., within one or more combination therapies to enhance antimicrobial activity), the one or more first functional groups can be characterized as a targeting moiety, dye, improved solubility agent, and/or structure-directing agent (e.g., micelle forming group). Further, example structures that can comprise the one or more first functional groups can include, but are not limited to: a benzyl group, mannose, galactose, glucose, biotin, folic acid, antibodies, peptide, a combination thereof, and/or the like.

The functionalized polycarbonate block can form a biodegradable molecular backbone. As shown in FIG. 1, the functionalized polycarbonate block can be functionalized with one or more quaternary ammonium functional groups to render the quaternary ammonium functionalized polycarbonate structure 102 cationic. The "n" can be an integer greater than or equal to 5 and less than or equal to. The one or quaternary ammonium functional groups can be linked to the one or more polycarbonate blocks via one or more linkage groups (e.g., represented by "X"). Example structures that can comprise the one or more linkage groups can include, but are not limited to: a butyl group, an ethyl group, a propyl group, a benzyl group, a combination thereof, and/or the like. Additionally, the one or more quaternary ammonium functional groups can comprise a third functional group (e.g., represented by "$R_3$"), a fourth functional group (e.g., represented by "$R_4$"), and/or a fifth functional group (e.g., represented by "$R_5$"). Example structures that can comprise the third, fourth, and/or fifth functional groups can include, but are not limited to: methyl groups, butyl groups, alkyl groups, hexane groups, phenyl groups, cyclohexyl groups, biphenyl groups, ethyl groups, alkyl and/or aryl groups containing 1 to 12 carbon atoms, ether groups, a combination thereof, and/or the like.

The second functional group (e.g., represented by "$R_2$") can be positioned at an opposite end of the functionalized polycarbonate block than the first functional group (e.g., represented by "$R_1$"). In one or more embodiments (e.g., within one or more combination therapies directed to enhance anticancer activity), the one or more second functional groups can be end groups that can also serve as spacers in stereocomplex embodiments. Further, example structures that can comprise the one or more second functional groups can include, but are not limited to: polylactic acid, polycaprolactone, polyvalerolactone, polycarbonate, polyethers, polyesters, a combination thereof, and/or the like. In one or more embodiments (e.g., within one or more combination therapies directed to enhance antimicrobial activity), the one or more second functional groups can be end groups including, but not limited to: a hydroxyl group, a hydrogen, one or more of the functional groups described herein, a combination thereof, and/or the like.

As shown in FIG. 1, the guanidinium functionalized polycarbonate structure 104 can comprise the functionalized polycarbonate block being functionalized by one or more functional guanidium groups. The one or more guanidinium functional groups can render the guanidinium functionalized polycarbonate structure 104 cationic. Further, the one or more guanidinium groups can be linked to the polycarbonate block via the one or more linage groups (e.g., represented by "X"). The "m" can be an integer greater than or equal to 5 and less than or equal to 75.

Also shown in FIG. 1, the quaternary ammonium and guanidinium functionalized polycarbonate structure 106 can comprise the functionalized polycarbonate block being functionalized by one or more quaternary ammonium functional groups and guanidium functional groups. The one or more quaternary ammonium functional groups and guanidinium functional groups can render the quaternary ammonium and guanidinium functionalized polycarbonate structure 106 cationic. The "g" can be an integer greater than or equal to 5 and less than or equal to 75. As shown in FIG. 1, the one or more quaternary ammonium functional groups can be linked to the one or more polycarbonate blocks via the one or more linkage groups (e.g., represented by "X"). Further, the one or more guanidinium functional groups can be bonded to the one or more quaternary ammonium functional groups via the one or more fifth functional groups.

In various embodiments, the quaternary ammonium functionalized polycarbonate structures 102 can exhibit antimicrobial and/or anticancer activities via one or more lytic mechanisms. In one or more embodiments, the guanidinium functionalized polycarbonate structures 104 can exhibit antimicrobial and/or anticancer activities via one or more translocation mechanisms. In some embodiments, the quaternary ammonium and guanidinium functionalized polycarbonate structures 106 can exhibit antimicrobial and/or anticancer activities via one or more lytic and/or translocation mechanisms.

Figure 2:
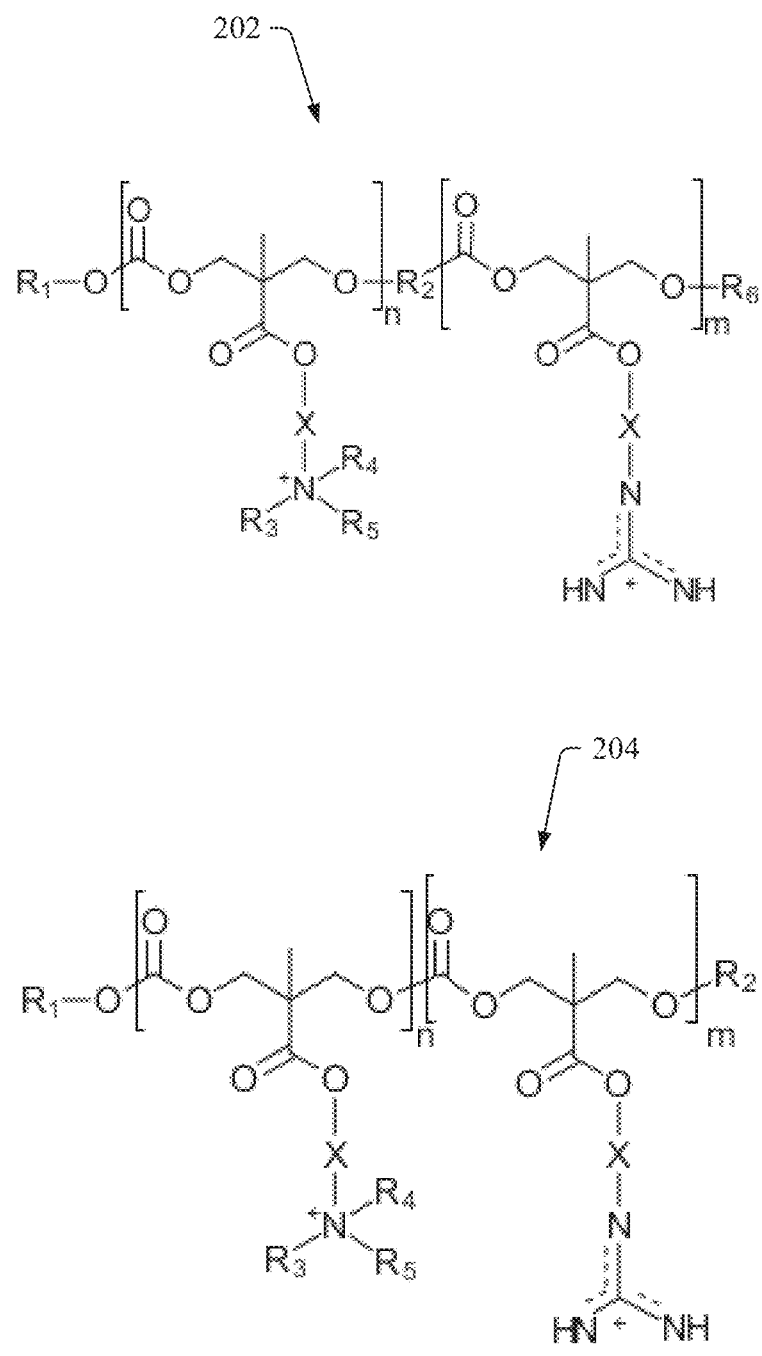
FIG. 2 illustrates a diagram of example, non-limiting chemical structures that can characterize antimicrobial and/or anticancer polymers in accordance with one or more embodiments described herein.

FIG. 2 illustrates a diagram of example, non-limiting chemical structures that can characterized one or more antimicrobial polymers and/or anticancer polymers that can form during a combination therapy that utilizes the one or more quaternary ammonium functionalized polycarbonates structures 102 and/or guanidinium functionalized polycarbonate structures 104 in accordance with one or more embodiments described herein. Repetitive description of like elements employed in other embodiments described herein is omitted for sake of brevity. In one or more embodiments, the one or more quaternary ammonium functionalized polycarbonate structures 102 and/or the one or more guanidinium functionalized polycarbonate structures 104 can self-assemble into well defined micelles (e.g., nanoparticles having a size greater than or equal to 1 nanometer and less than or equal to 100 nm).

Additionally, in various embodiments, one or more combination therapies comprising the use of both the one or more quaternary ammonium functionalized polycarbonate structures 102 and guanidinium functionalized polycarbonate structures 104 can result in one or more stereocomplexes of the functionalized polycarbonates. For example, FIG. 2 illustrates a first copolymer structure 202 that can exemplify self assembly of the one or more quaternary ammonium functionalized polycarbonate structures 102 with the one or more guanidinium functionalized polycarbonate structures 104. Within the first copolymer structure 202, the second functional group (e.g., represented by "$R_2$") can serve as a spacer (e.g., a polylactic acid spacer) between the one or more quaternary ammonium functionalized polycarbonate blocks and/or the guanidinium functionalized polycarbonate blocks. Further, the first copolymer 202 can comprise a sixth functional group (e.g., represented by "$R_6$") that can be an end group including, but not limited to: hydrogen, a hydroxyl group, a combination thereof, and/or the like. For example, the first copolymer structure 202 can be a nanosize (e.g., having a size greater than or equal to 1 nm and less than or equal to 100 nm) stereocomplex with kinetic stability enhanced by the one or more second functional groups. In various embodiments, the first copolymer structure 202 can be formed in one or more combination therapies to treat one or more cancers (e.g., inhibit the growth of cancer cells).

In another example, FIG. 2 illustrates a second copolymer structure 204 that can exemplify self assembly of the one or more quaternary ammonium functionalized polycarbonate structures 102 with the one or more guanidinium functionalized polycarbonate structures 104. Within the second copolymer structure 204, the one or more quaternary ammonium functionalized polycarbonate blocks can be directly bonded to the one or more guanidinium functionalized polycarbonate blocks. For instance, the second functional group (e.g., a hydrogen) of one or more of the functionalized polycarbonate blocks can be replaced by one or more other functionalized polycarbonate blocks to facilitate a block copolymer or a random block copolymer. In various embodiments, the second copolymer structure 204 can be sub-nanosize (e.g., having a size less than 1 nm) and/or formed in one or more combination therapies to treat one or more microbial infections (e.g., inhibit the growth of bacteria).

Figure 3:
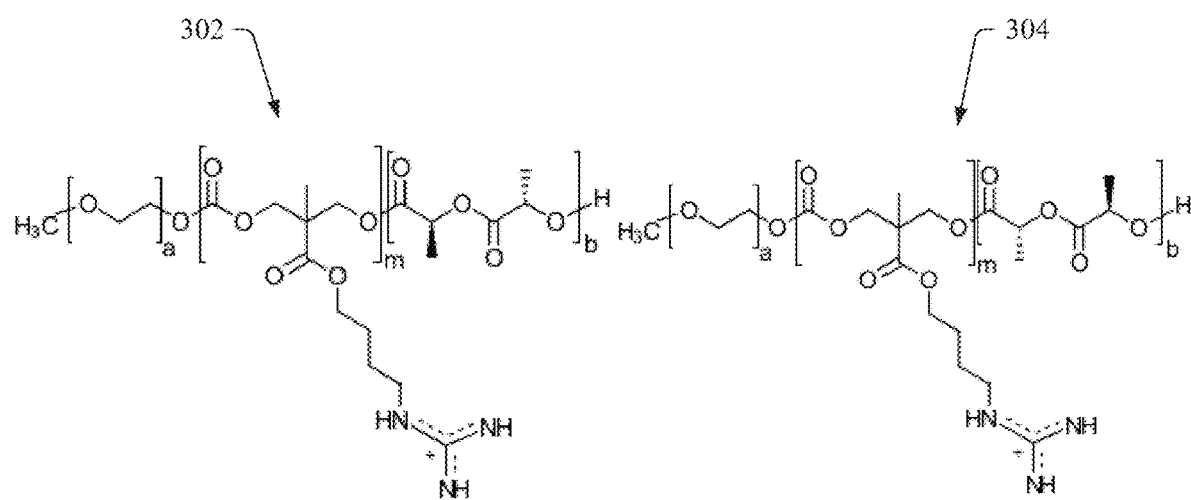
FIG. 3 illustrates a diagram of example, non-limiting triblock polymers comprising a guanidinium functionalized block that can be comprised within a chemical composition to facilitate one or more combination therapies in accordance with one or more embodiments described herein.

FIG. 3 illustrates a diagram on example, non-limiting chemical structures that can exemplify the one or more guanidinium functionalized polycarbonate structures 104 that can be utilized in combination with one or more other polymers and/or chemotherapeutic agents in one or more combination therapies directed against one or more microbes (e.g., one or more antimicrobial resistant bacteria) and/or cancer cells in accordance with one or more embodiments. Repetitive description of like elements employed in other embodiments described herein is omitted for sake of brevity. In various embodiments, the one or more guanidinium functionalized polycarbonate structures 104, such as the examples depicted in FIG. 3, can exhibit antimicrobial and/or anticancer activity via a translocation mechanism.

As shown in FIG. 3, the one or more example guanidinium functionalized polycarbonates can be triblock copolymers with a biodegradable molecular backbone comprising a polyethylene glycol ("PEG") block (e.g., corresponding to the first functional group), a guanidinium functionalized polycarbonate block, and a polylactic acid block (e.g., corresponding to the second functional group). In various embodiments, the PEG block can have an average molecular weight that is greater than or equal to 2,000 daltons (Da) and less than or equal to 20,000 da. Further, "a" can represent an integer greater than or equal to 45 and less than or equal to 450; and "b" can represent an integer greater than or equal to 7 and less than or equal to 100. Additionally, as shown in FIG. 3, the linkage group can be a butyl group in the exemplary guanidinium functionalized polycarbonates.

In one or more embodiments, the one or more exemplary guanidinium functionalized polycarbonates can self-assemble into well defined micelles (e.g., nanoparticles having a size greater than or equal to 1 nanometer and less than or equal to 100 nanometers). Additionally, the polylactic acid block can serve as a spacer to enhance kinetic stability. As shown in FIG. 3, a first example guanidinium functionalized polycarbonate 302 can exemplify the guanidinium functionalized polycarbonate structure 104 and/or can include a poly-L-lactic acid ("PLLA") block. Also, a second example guanidinium functionalized polycarbonate 304 can also exemplify the guanidinium functionalized polycarbonate structure 104 and/or can include a poly-D-lactic acid ("PDLA") block.

Figure 4:
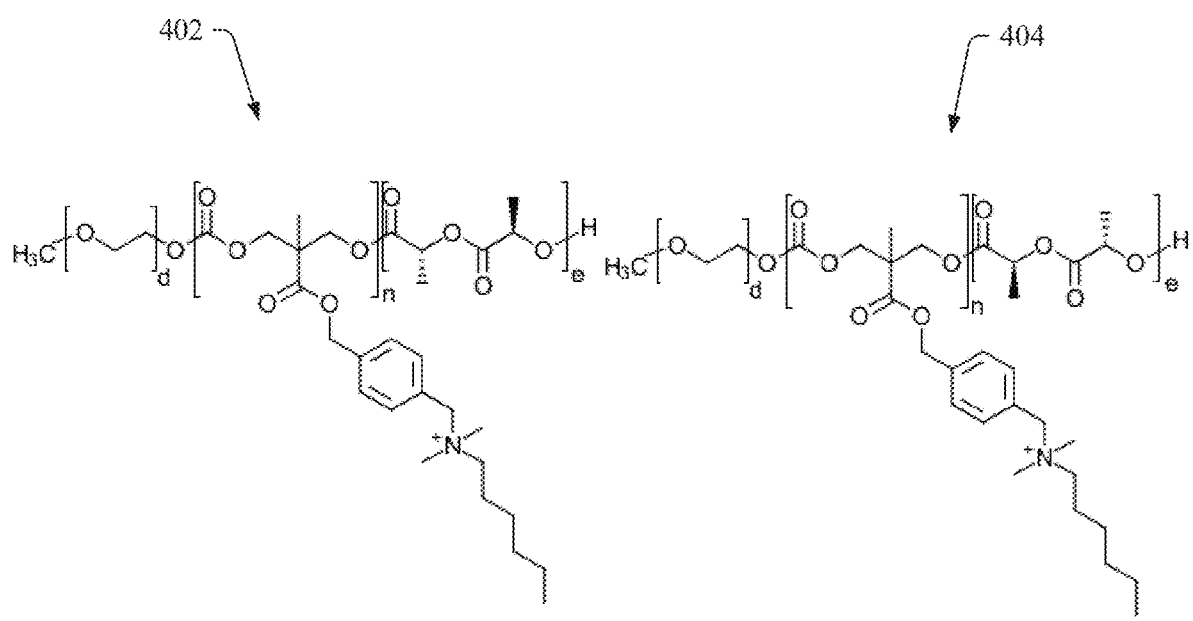
FIG. 4 illustrates a diagram of example, non-limiting triblock polymers comprising a quaternary ammonium functionalized block that can be comprised within a chemical composition to facilitate one or more combination therapies in accordance with one or more embodiments described herein.

FIG. 4 illustrates a diagram on example, non-limiting chemical structures that can exemplify the one or more quaternary ammonium functionalized polycarbonate structures 102 that can be utilized in combination with one or more other polymers and/or chemotherapeutic agents in one or more combination therapies directed against one or more microbes (e.g., one or more antimicrobial resistant bacteria) and/or cancer cells in accordance with one or more embodiments. Repetitive description of like elements employed in other embodiments described herein is omitted for sake of brevity. In various embodiments, the one or more example quaternary ammonium functionalized polycarbonates can exhibit antimicrobial and/or anticancer activity via a lytic mechanism.

As shown in FIG. 4, the one or more example quaternary ammonium functionalized polycarbonates can be triblock copolymers with a biodegradable molecular backbone comprising a PEG block (e.g., corresponding to the first functional group), a quaternary ammonium functionalized polycarbonate block, and a polylactic acid block (e.g., corresponding to the second functional group). In various embodiments, the PEG block can have an average molecular weight that is greater than or equal to 2,000 Da and less than or equal to 20,000 Da. The "d" can represent an integer greater than or equal to 45 and less than or equal to 450; and "e" can represent an integer greater than or equal to 7 and less than or equal to 100. Additionally, as shown in FIG. 4, the linkage group can be a benzyl group in the exemplary quaternary ammonium functionalized polycarbonates. Also shown in FIG. 4, the exemplary quaternary ammonium functionalized polycarbonates can comprise a quaternary ammonium functional group having a first methyl group (e.g., corresponding to the third functional group), a second methyl group (e.g., corresponding to the fourth functional group), and/or a hexane group (e.g., corresponding to the fifth functional group).

In one or more embodiments, the one or more example quaternary ammonium functionalized polycarbonates can self-assemble into well defined micelles (e.g., nanoparticles having a size greater than or equal to 1 nanometer and less than or equal to 100 nanometers). Additionally, the polylactic acid block can serve as a spacer to enhance kinetic stability (e.g., with regards to one or more stereocomplexes). As shown in FIG. 4, a first example quaternary ammonium functionalized polycarbonate 402 can exemplify the one or more quaternary ammonium and guanidinium functionalized polycarbonate structure 106 and can include a PDLA block. Also, a second example quaternary ammonium functionalized polycarbonate 404 can include a PLLA block.

Figure 5:
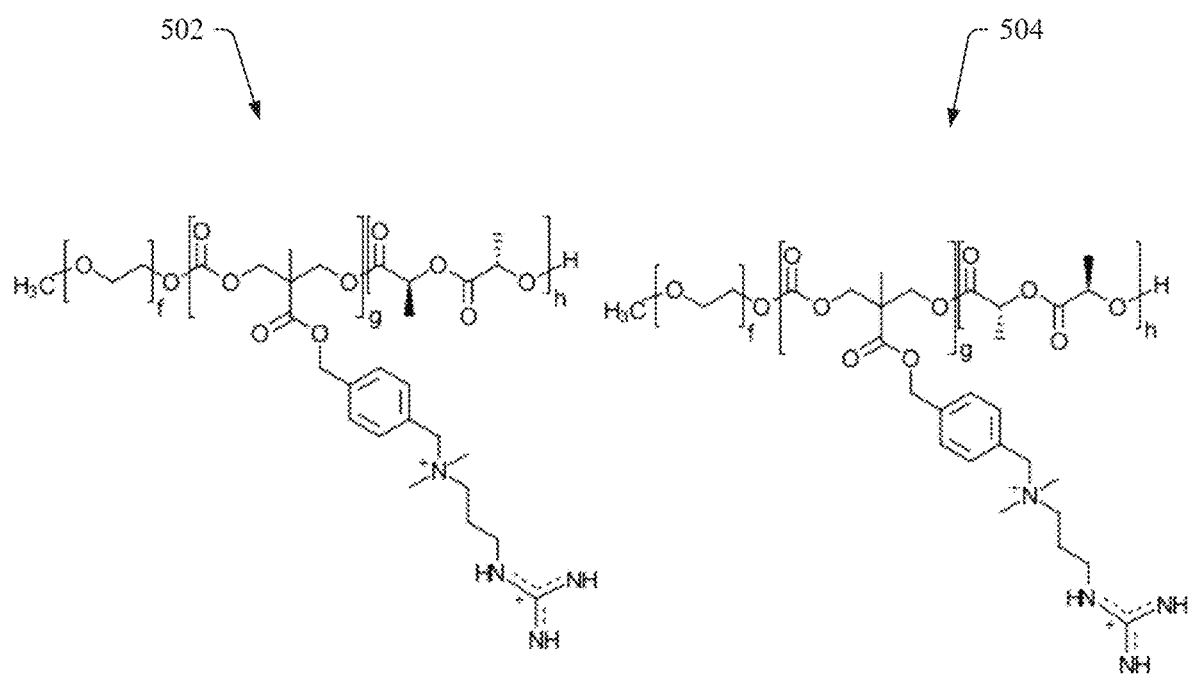
FIG. 5 illustrates a diagram of example, non-limiting triblock polymers comprising a guanidinium and quaternary ammonium functionalized block that can be comprised within a chemical composition to facilitate one or more combination therapies in accordance with one or more embodiments described herein.

FIG. 5 illustrates a diagram on example, non-limiting chemical structures that can exemplify the one or more quaternary ammonium and guanidinium functionalized polycarbonate structure 106 that can be utilized in combination with one or more other polymers and/or chemotherapeutic agents in one or more combination therapies directed against one or more microbes (e.g., one or more antimicrobial resistant bacteria) and/or cancer cells in accordance with one or more embodiments. Repetitive description of like elements employed in other embodiments described herein is omitted for sake of brevity. In various embodiments, the one or more example quaternary ammonium and guanidinium functionalized polycarbonates can exhibit antimicrobial and/or anticancer activity via a lytic and/or translocation mechanism.

As shown in FIG. 5, the one or more example quaternary ammonium and guanidinium functionalized polycarbonates can be triblock copolymers with a biodegradable molecular backbone comprising a PEG block (e.g., corresponding to the second functional group), a quaternary ammonium and guanidinium functionalized polycarbonate block, and a polylactic acid block (e.g., corresponding to a second functional group). In various embodiments, the PEG block can have an average molecular weight that is greater than or equal to 2,000 Da and less than or equal to 20,000 Da. The "f" can represent an integer greater than or equal to 45 and less than or equal to 450; and "h" can represent an integer greater than or equal to 7 and less than or equal to 100.

In various embodiments, the one or more polycarbonate blocks can be functionalized with both a quaternary ammonium functional group and a guanidinium functional group (e.g., comprised on the same molecular branch). Further, the quaternary ammonium functional group can facilitate one or more lytic mechanism performed by the polymer and/or the guanidinium functional group can facilitate one or more translocation mechanisms performed by the polymer.

In one or more embodiments, the one or more example quaternary ammonium and guanidinium functionalized polycarbonates can self-assemble into well defined micelles (e.g., nanoparticles having a size greater than or equal to 1 nanometer and less than or equal to 100 nanometers). Additionally, the polylactic acid block can serve as a spacer to enhance kinetic stability. As shown in FIG. 5, a first example quaternary ammonium and guanidinium functionalized polycarbonates 502 exemplify the quaternary ammonium and guanidinium functionalized polycarbonate structures 106 and can include a PLLA block. Also, a second example quaternary ammonium and guanidinium functionalized polycarbonate 504 can include a PDLA block. Further, the first and second example quaternary ammonium and guanidinium functionalized polycarbonates 502, 504 can comprise a benzyl aryl linkage group and/or a propyl fifth functional group.

Figure 6:
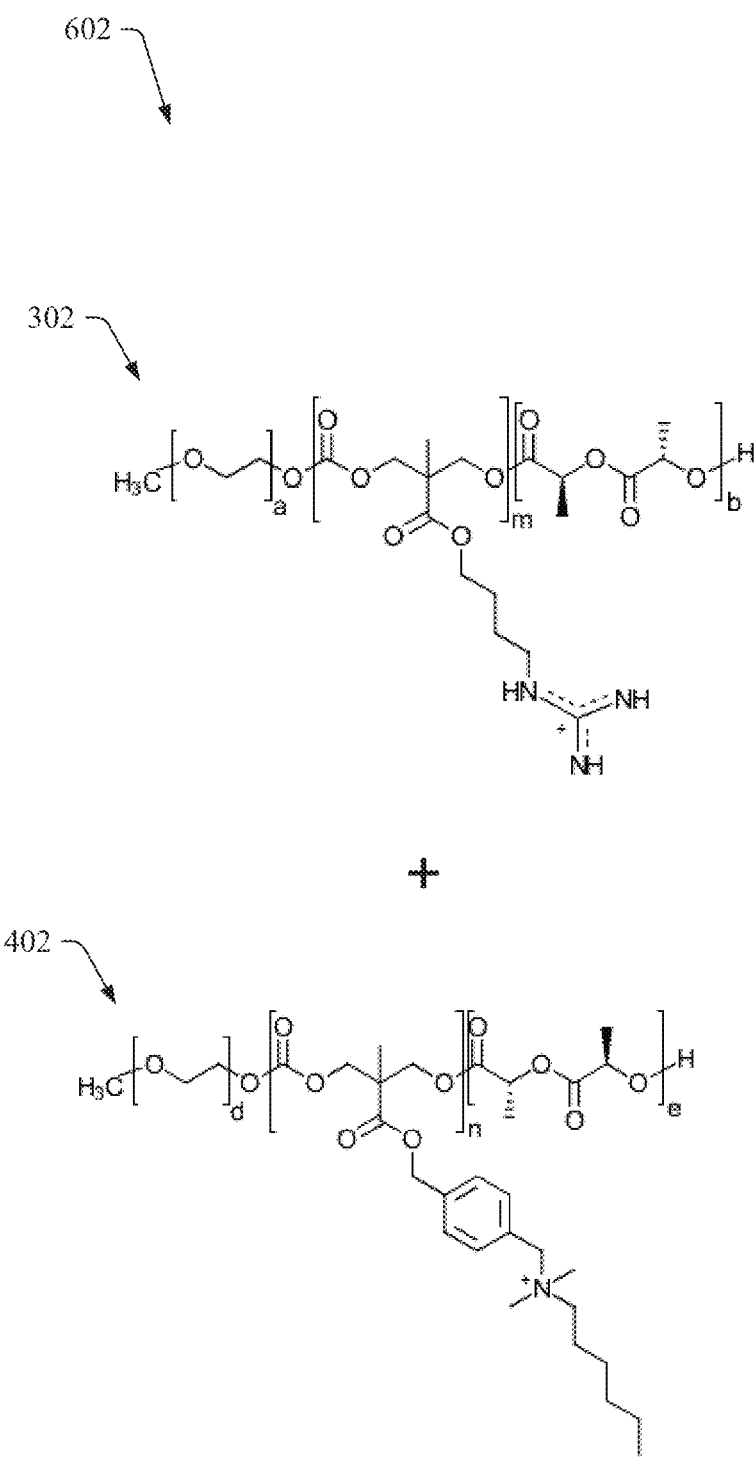
FIG. 6 illustrates a diagram of an example, non-limiting stereocomplex copolymer that can exhibit anticancer activity in accordance with one or more embodiments described herein.

FIG. 6 illustrates a diagram of a non-limiting example stereocomplex 602 that can form from a combination therapy of the one or more quaternary ammonium functionalized polycarbonate structures 102 and guanidinium functionalized polycarbonate structures 104 directed against one or more microbes (e.g., one or more antimicrobial resistant bacteria) and/or cancer cells in accordance with one or more embodiments. Repetitive description of like elements employed in other embodiments described herein is omitted for sake of brevity. In various embodiments, the example stereocomplex 602 can exhibit anticancer activity via a synergistic effect between lytic and translocation mechanisms. As shown in FIG. 6, one or more combination therapies described herein can comprise one or more stereocomplexes constituted from a mix of the one or more of the polycarbonates described herein that form stabilized micelles. For example, the example stereocomplex 602 results from a mix of the first example guanidinium functionalized polycarbonate 302 and the first example quaternary ammonium functionalized polycarbonate 402. One of ordinary skill in the art will recognize that other stereocomplexes are also envisaged that embody one or more other mixtures of the example polycarbonate polymers described herein (e.g., mixtures of the chemical structures depicted in FIG. 1).

Figure 7A:
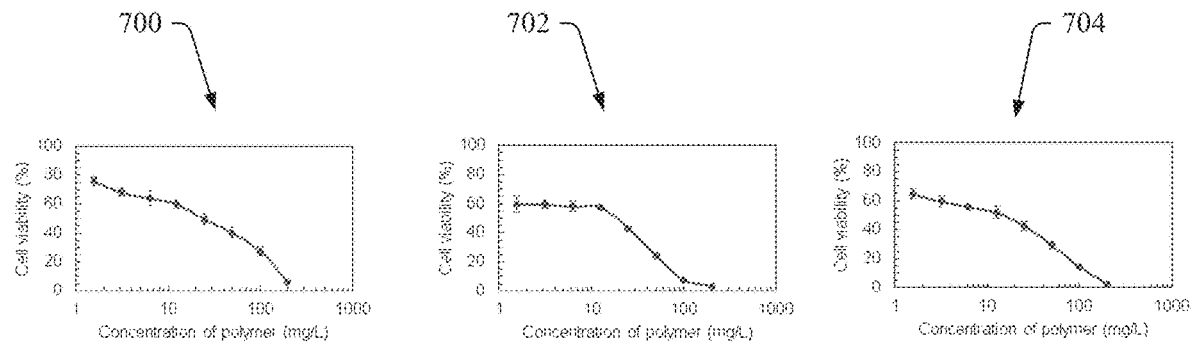
FIGS. 7A-7B illustrate diagrams of example, non-limiting cytotoxicity graphs that can depict the efficacy of anticancer activity exhibited by one or more triblock polymers comprising a guanidinium functionalized block in accordance with one or more embodiments described herein.
Figure 7B:
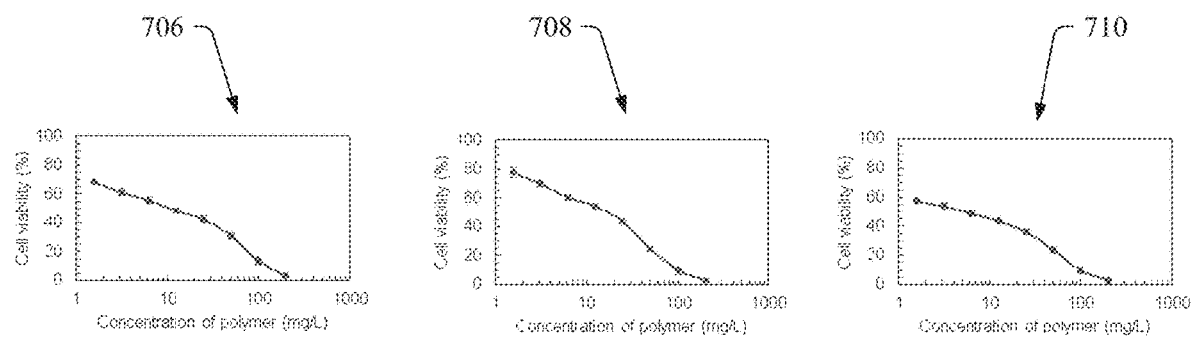

FIGS. 7A and 7B can illustrate diagrams of example, non-limiting cytotoxicity graphs regarding the guanidinium functionalized polycarbonate structures 104 against HCC827 human lung adenocarcinoma cell line in accordance with one or more embodiments described herein. Repetitive description of like elements employed in other embodiments described herein is omitted for sake of brevity. FIG. 7A can depict the cytotoxicity of the guanidinium functionalized polycarbonate structures 104 after 24 hours of treatment, and FIG. 7B can depict the cytotoxicity of the guanidinium functionalized polycarbonate structures 104 after 48 hours of treatment. As shown in FIGS. 7A and/or 7B, the one or more guanidinium functionalized polycarbonate structures 104 described herein can exhibit anticancer activity.

Cytotoxicity graph 700 regards a micellar formation of the first example guanidinium functionalized polycarbonate 302; wherein the PEG block has an average molecular weight of 5,000 Daltons (Da), "m" is 40, and "b" is 23. As shown in cytotoxicity graph 700, the half maximal inhibitory concentration ("$IC_{50}$") of the given first example guanidinium functionalized polycarbonate 302 against HCC827 is 24.4 mg/L after 24 hours of treatment. Cytotoxicity graph 702 regards a micellar formation of the second example guanidinium functionalized polycarbonate 304; wherein the PEG block has an average molecular weight of 5,000 Da, "m" is 43, and "b" is 23. As shown in cytotoxicity graph 702, the $IC_{50}$ of the given second example guanidinium functionalized polycarbonate 304 against HCC827 is 19.2 mg/L after 24 hours of treatment. Further, cytotoxicity graph 704 regards an example stereocomplex formed from a mix of the first example guanidinium functionalized polycarbonate 302 (e.g., wherein the PEG block has an average molecular weight of 5,000 Daltons (Da), "m" is 40, and "b" is 23) and the second example guanidinium functionalized polycarbonate 304 (e.g., wherein the PEG block has an average molecular weight of 5,000 Da, "m" is 43, and "b" is 23). As shown in cytotoxicity graph 704, the $IC_{50}$ of the given stereocomplex against HCC827 is 15.3 mg/L after 24 hours of treatment. FIG. 7A exemplifies that the stereocomplex (e.g., a mixture of the first and second example guanidinium functionalized polycarbonates 302, 304) can exhibit stronger anticancer activity than the respective micellar formations.

Cytotoxicity graph 706 further regards the micellar formation of the first example guanidinium functionalized polycarbonate 302; wherein the PEG block has an average molecular weight of 5,000 Daltons (Da), "n" is 40, and "p" is 23. As shown in cytotoxicity graph 706, the $IC_{50}$ of the given first example guanidinium functionalized polycarbonate 302 against HCC827 is 10.8 mg/L after 48 hours of treatment. Cytotoxicity graph 708 further regards the micellar formation of the second example guanidinium functionalized polycarbonate 304; wherein the PEG block has an average molecular weight of 5,000 Da, "n" is 43, and "p" is 23. As shown in cytotoxicity graph 708, the $IC_{50}$ of the given second example guanidinium functionalized polycarbonate 304 against HCC827 is 17.0 mg/L after 48 hours of treatment. Additionally, cytotoxicity graph 710 further regards the stereocomplex chemical composition formed from a mixture of the first example guanidinium functionalized polycarbonate 302 (e.g., wherein the PEG block has an average molecular weight of 5,000 Da, "n" is 40, and "p" is 23) and the second example guanidinium functionalized polycarbonate 304 (e.g., wherein the PEG block has an average molecular weight of 5,000 Da, "n" is 43, and "p" is 23). As shown in cytotoxicity graph 710, the $IC_{50}$ of the given stereocomplex against HCC827 is 5.5 mg/L after 48 hours of treatment. FIG. 7B exemplifies that the example guanidinium functionalized polycarbonates 302, 304 and/or mixtures thereof can exhibit anticancer activity that increases over time. The $IC_{50}$ values in cytotoxicity graphs 700, 702, and 704 were determined from a single experiment.

Figure 8A:
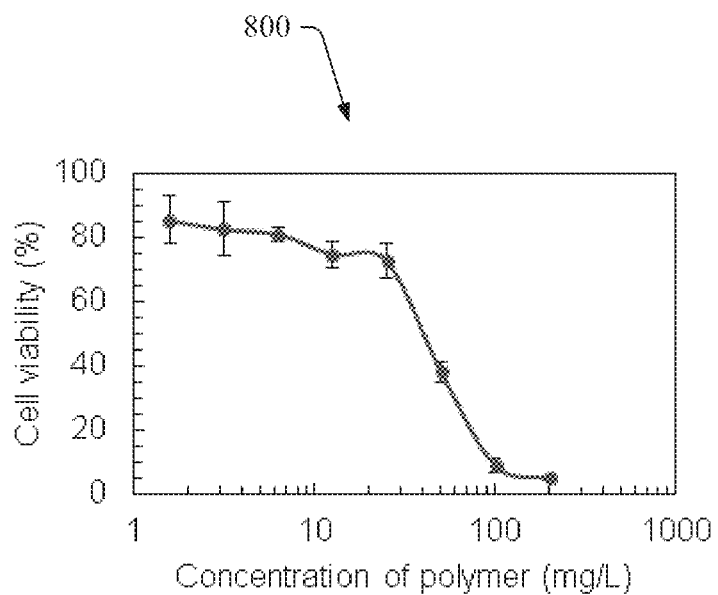
FIG. 8A-8B illustrate diagrams of example, non-limiting cytotoxicity graphs that can depict the efficacy of anticancer activity exhibited by one or more triblock polymers comprising a quaternary ammonium functionalized block in accordance with one or more embodiments described herein.
Figure 8B:
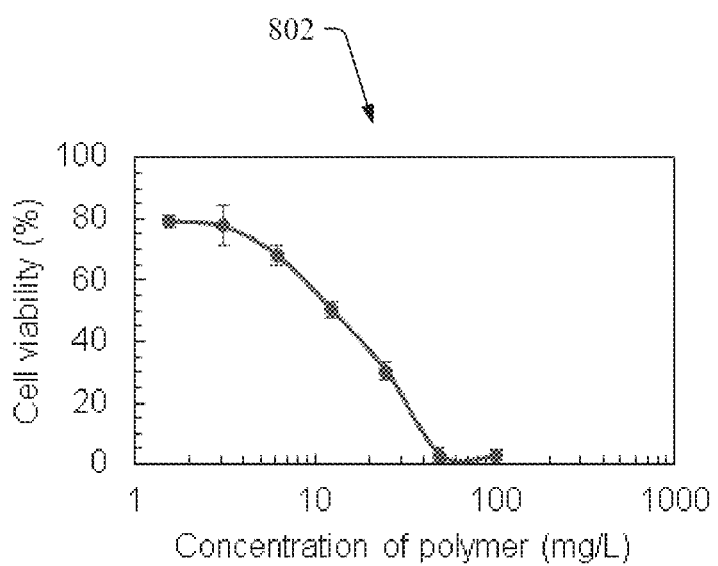

FIGS. 8A and 8B can illustrate diagrams of example, non-limiting cytotoxicity graphs regarding the quaternary ammonium functionalized polycarbonate structures 102 against HCC827 human lung adenocarcinoma cell line in accordance with one or more embodiments described herein. Repetitive description of like elements employed in other embodiments described herein is omitted for sake of brevity. FIG. 8A can depict the cytotoxicity of the quaternary ammonium functionalized polycarbonate structures 102 after 24 hours of treatment, and FIG. 8B can depict the cytotoxicity of the quaternary ammonium functionalized polycarbonate structures 102 after 48 hours of treatment. As shown in FIGS. 8A and/or 8B, the one or more quaternary ammonium functionalized polycarbonate structures 102 described herein can exhibit anticancer activity.

Cytotoxicity graph 800 regards a micellar formation of the first example quaternary ammonium functionalized polycarbonate 402; wherein the PEG block has an average molecular weight of 5,000 Da, "n" is 43, and "e" is 20. As shown in cytotoxicity graph 800, the $IC_{50}$ of the given first example quaternary ammonium functionalized polycarbonate 402 against HCC827 is 39.8 mg/L after 24 hours of treatment. Cytotoxicity graph 802 further regards the micellar formation of the first example quaternary ammonium functionalized polycarbonate 402; wherein the PEG block has an average molecular weight of 5,000 Da, "n" is 43, and "p" is 20. As shown in cytotoxicity graph 802, the $IC_{50}$ of the given first example quaternary ammonium functionalized polycarbonate 402 against HCC827 is 25.0 mg/L after 48 hours of treatment. FIG. 8B exemplifies that the example quaternary ammonium functionalized polycarbonate 402 and/or mixtures thereof can exhibit anticancer activity that increases over time. The $IC_{50}$ values in cytotoxicity graphs 800 and 802 were determined from a single experiment.

Figure 9A:
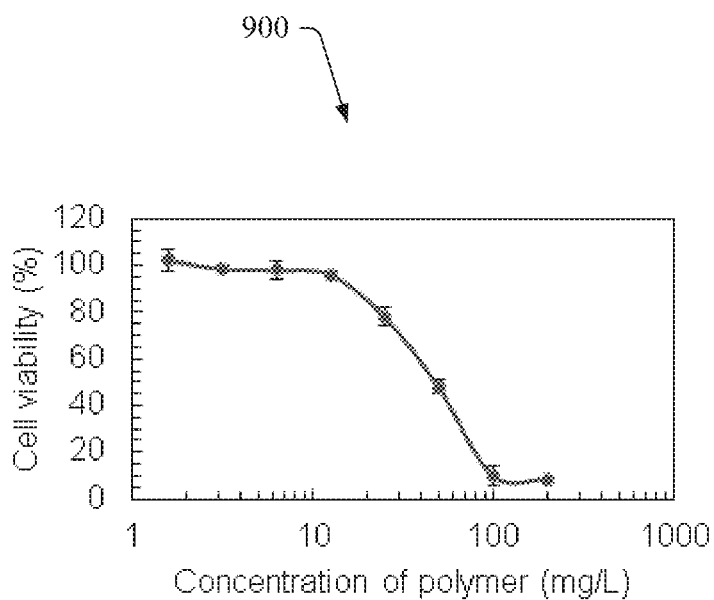
FIGS. 9A-9B illustrate diagrams of example, non-limiting cytotoxicity graphs that can depict the efficacy of anticancer activity exhibited by one or more triblock polymers comprising a guanidinium functionalized and quaternary ammonium functionalized block in accordance with one or more embodiments described herein.
Figure 9B:
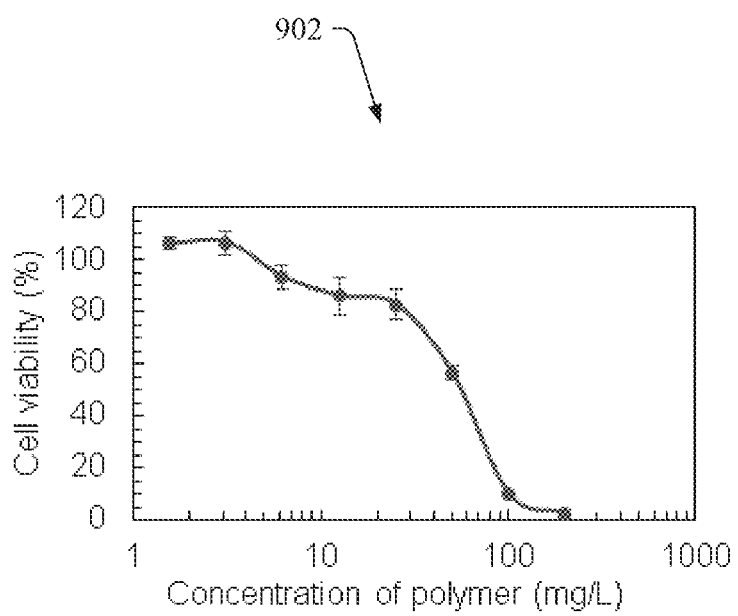

FIGS. 9A and 9B can illustrate diagrams of example, non-limiting cytotoxicity graphs regarding the quaternary ammonium and guanidinium functionalized polycarbonate structures 106 against HCC827 human lung adenocarcinoma cell line in accordance with one or more embodiments described herein. Repetitive description of like elements employed in other embodiments described herein is omitted for sake of brevity. FIG. 9A can depict the cytotoxicity of the quaternary ammonium and guanidinium functionalized polycarbonate structures 106 after 24 hours of treatment, and FIG. 9B can depict the cytotoxicity of the quaternary ammonium and guanidinium functionalized polycarbonate structures 106 after 48 hours of treatment. As shown in FIGS. 9A and/or 9B, the one or more quaternary ammonium and guanidinium functionalized polycarbonate structures 106 described herein can exhibit anticancer activity.

Cytotoxicity graph 900 regards a micellar formation of the second example quaternary ammonium and guanidinium functionalized polycarbonate 504; wherein the PEG block has an average molecular weight of 5,000 Da, "g" is 40, and "h" is 20. As shown in cytotoxicity graph 900, the $IC_{50}$ of the given second example quaternary ammonium functionalized polycarbonate 504 against HCC827 is 48.9 mg/L after 24 hours of treatment. Cytotoxicity graph 902 further regards the micellar formation of the second example quaternary ammonium and guanidinium functionalized polycarbonate 504; wherein the PEG block has an average molecular weight of 5,000 Da, "g" is 40, and "h" is 20. As shown in cytotoxicity graph 902, the $IC_{50}$ of the given second example quaternary ammonium and guanidinium functionalized polycarbonate 504 against HCC827 is 56.0 mg/L after 48 hours of treatment. The $IC_{50}$ values in cytotoxicity graphs 900 and 902 were determined from a single experiment.

Figure 10A:
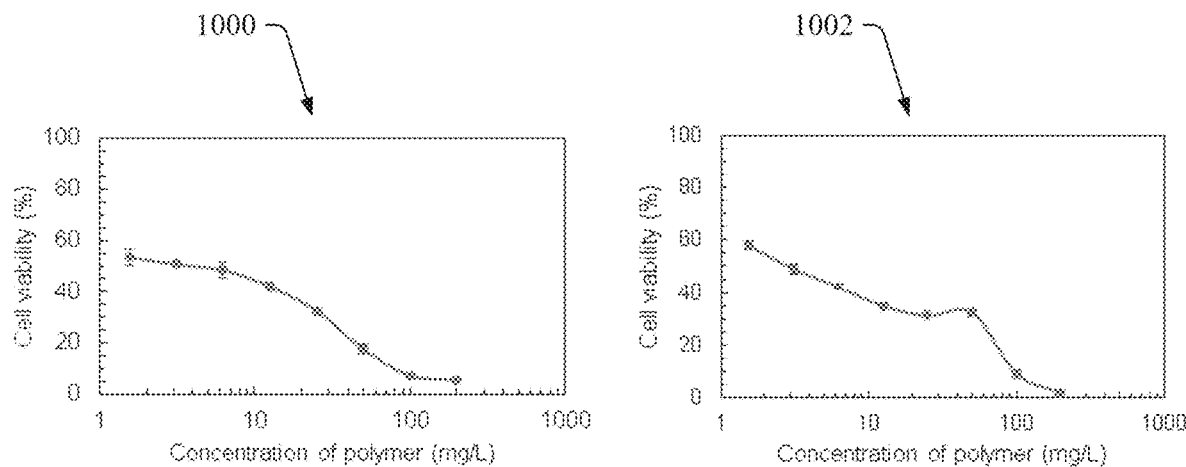
FIGS. 10A-10B illustrate diagrams of example, non-limiting cytotoxicity graphs that can depict the efficacy of anticancer activity exhibited by a chemical composition comprising a first triblock polymer having a guanidinium functionalized block and a second triblock polymer having a quaternary ammonium functionalized block in accordance with one or more embodiments described herein.
Figure 10B:
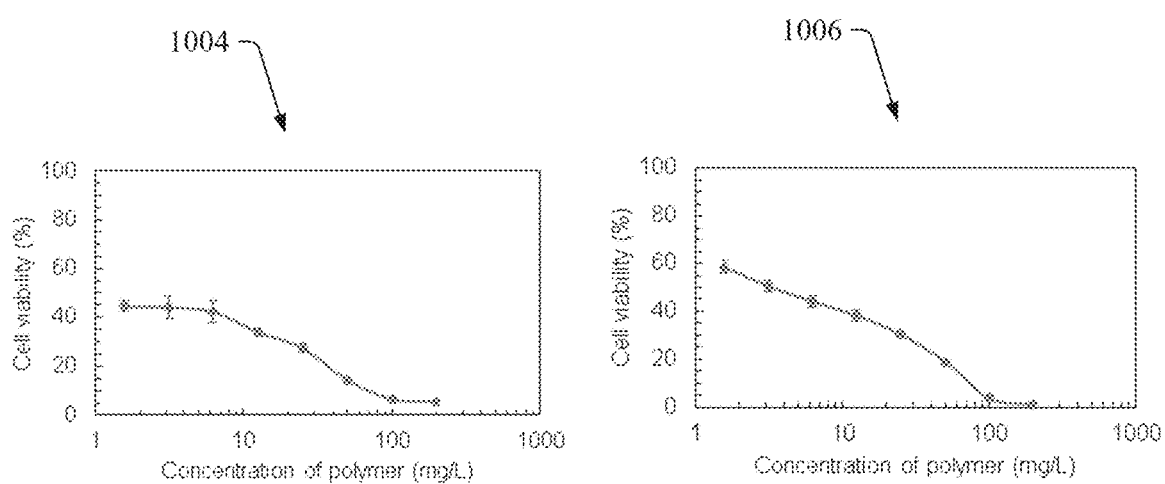

FIGS. 10A and 10B can illustrate diagrams of example, non-limiting cytotoxicity graphs regarding a combination therapy using a chemical composition that includes a stereocomplex formation of the quaternary ammonium functionalized polycarbonate structures 102 mixed with the guanidinium functionalized polycarbonate structures 104 against HCC827 and A459 human lung adenocarcinoma cell lines in accordance with one or more embodiments described herein. Repetitive description of like elements employed in other embodiments described herein is omitted for sake of brevity. FIG. 10A can depict the cytotoxicity of the stereocomplex after 24 hours of treatment, and FIG. 10B can depict the cytotoxicity of the stereocomplex after 48 hours of treatment. As shown in FIGS. 10A and/or 10B, the stereocomplexes of the one or more quaternary ammonium functionalized polycarbonate structures 102 mixed with the one or more guanidinium functionalized polycarbonate structures 104 can exhibit greater anticancer activity than that of the respective micellar formations of the triblock copolymers.

Cytotoxicity graph 1000 regards the example stereocomplex 602; wherein the PEG block has an average molecular weight of 5,000 Da, "m" is 40, "b" is 23, "n" is 43, and "e" is 20. As shown in cytotoxicity graph 1000, the $IC_{50}$ of the example stereocomplex 602 against HCC827 is 1.7 mg/L after 24 hours of treatment. Cytotoxicity graph 1002 further the example stereocomplex 602; wherein the PEG block has an average molecular weight of 5,000 Da, "m" is 40, "b" is 23, "n" is 43, and "e" is 20. As shown in cytotoxicity graph 1002, the $IC_{50}$ of the example stereocomplex copolymer against A549 is 2.9 mg/L after 24 hours of treatment. The $IC_{50}$ values in cytotoxicity graphs 1000 and 1002 were determined from a single experiment. FIG. 10A exemplifies that the example stereocomplex 602 can exhibit stronger anticancer activity than the respective micellar formations (e.g., micelles of the first example guanidinium functionalized polycarbonate 302, as exhibited in FIG. 7A; or micelles of the first example quaternary ammonium functionalized polycarbonate 402, as exhibited in FIG. 8A).

Additionally, cytotoxicity graph 1004 further regards the example stereocomplex 602; wherein the PEG block has an average molecular weight of 5,000 Da, "m" is 40, "b" is 23, "n" is 43, and "e" is 20. As shown in cytotoxicity graph 1004, the $IC_{50}$ of the example stereocomplex 602 against HCC827 is 1.3 mg/L after 48 hours of treatment. Additionally, cytotoxicity graph 1006 further the example stereocomplex 602; wherein the PEG block has an average molecular weight of 5,000 Da, "m" is 40, "b" is 23, "n" is 43, and "e" is 20. As shown in cytotoxicity graph 1006, the $IC_{50}$ of the example stereocomplex 602 against A549 is 3.1 mg/L after 48 hours of treatment. The $IC_{50}$ values in cytotoxicity graphs 1004 and 1006 were determined from a single experiment. FIG. 10B exemplifies that the first copolymer structures 202 can exhibit anticancer activity that increases over time. Further, the similar $IC_{50}$ values achieved after 24 hours and 48 hours can indicate that a combination therapy utilizing the first copolymer structures 202 (e.g., example stereocomplex 602) can exert anticancer function rapidly.

Figure 11A:
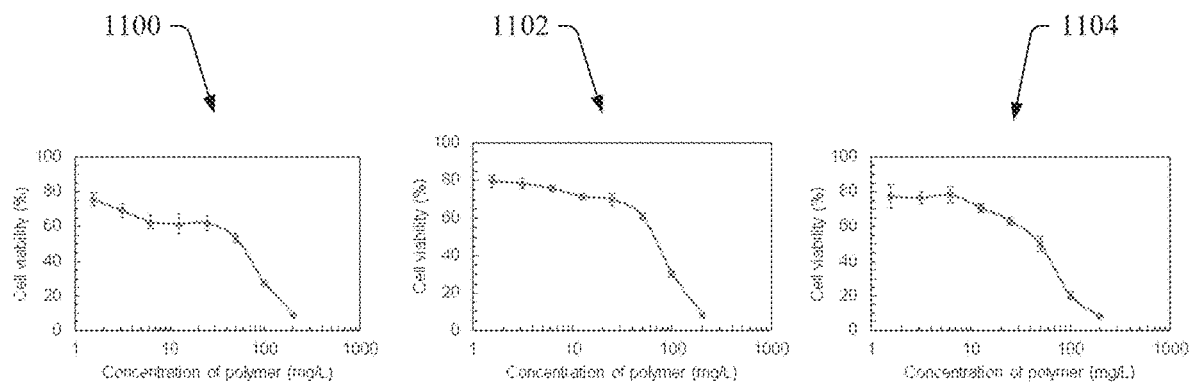
FIGS. 11A-11B illustrate diagrams of example, non-limiting cytotoxicity graphs that can depict the efficacy of anticancer activity exhibited by one or more triblock polymers comprising a guanidinium functionalized block and a polylactic acid block at various lengths in accordance with one or more embodiments described herein.
Figure 11B:
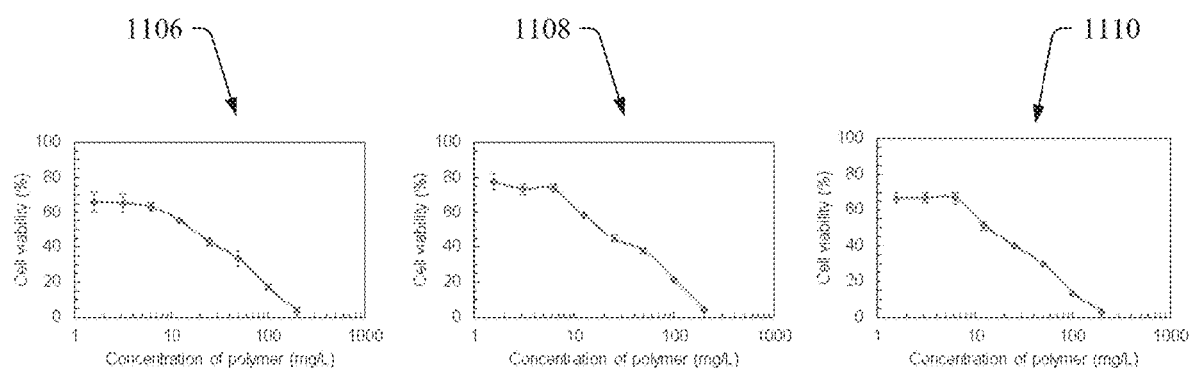

FIGS. 11A and 11B can illustrate diagrams of example, non-limiting cytotoxicity graphs regarding an effect that the length of the second functional group (e.g., the polylactic acid blocks) has on the anticancer activity of the described antimicrobial and/or anticancer polymers in accordance with one or more embodiments described herein. Repetitive description of like elements employed in other embodiments described herein is omitted for sake of brevity. FIG. 11A can depict the cytotoxicity of the first example guanidinium functionalized polycarbonate 302, the second example guanidinium functionalized polycarbonate 304, and/or mixtures thereof after 24 hours of treatment against HCC827. FIG. 11B can depict the first example guanidinium functionalized polycarbonate 302, the second example guanidinium functionalized polycarbonate 304, and/or mixtures thereof after 48 hours of treatment against HCC827. The cytotoxicity graphs of FIGS. 11A and/or 11B can regard micelles and/or stereocomplexes having longer second functional groups (e.g., polylactic acid blocks) than the micelles and/or stereocomplexes analyzed by FIGS. 7A and/or 7B.

Cytotoxicity graph 1100 regards a micellar formation of the first example guanidinium functionalized polycarbonate 302; wherein the PEG block has an average molecular weight of 5,000 Da, "m" is 40, and "b" is 40. As shown in cytotoxicity graph 1100, the $IC_{50}$ of the given first example guanidinium functionalized polycarbonate 302 against HCC827 can be 56.0 mg/L after 24 hours of treatment. Cytotoxicity graph 1102 regards a micellar formation of the second example guanidinium functionalized polycarbonate 304; wherein the PEG block has an average molecular weight of 5,000 Da, "m" is 43, and "b" is 40. As shown in cytotoxicity graph 1102, the $IC_{50}$ of the given second example guanidinium functionalized polycarbonate 304 against HCC827 can be 65.5 mg/L after 24 hours of treatment. Further, cytotoxicity graph 1104 regards a stereocomplex chemical composition formed from a mixture of the first example guanidinium functionalized polycarbonate 302 (e.g., wherein the PEG block has an average molecular weight of 5,000 Da, "m" is 40, and "b" is 40) and the second example guanidinium functionalized polycarbonate 304 (e.g., wherein the PEG block has an average molecular weight of 5,000 Da, "m" is 43, and "b" is 40). The $IC_{50}$ values in cytotoxicity graphs 1100, 1102, and 1104 were determined from a single experiment. As shown in cytotoxicity graph 1104, the $IC_{50}$ of the given stereocomplex against HCC827 can be 49.8 mg/L after 24 hours of treatment. FIG. 11A exemplifies that the stereocomplex (e.g., a mixture of the first and second example guanidinium functionalized polycarbonates 302, 304) can exhibit stronger anticancer activity than the respective micellar formations.

Cytotoxicity graph 1106 further regards the micellar formation of the first example guanidinium functionalized polycarbonate 302; wherein the PEG block has an average molecular weight of 5,000 Da, "m" is 40, and "b" is 40. As shown in cytotoxicity graph 1106, the $IC_{50}$ of the given first example guanidinium functionalized polycarbonate 302 against HCC827 can be 16.5 mg/L after 48 hours of treatment. Cytotoxicity graph 1108 further regards the micellar formation of the second example guanidinium functionalized polycarbonate 304; wherein the PEG block has an average molecular weight of 5,000 Da, "m" is 43, and "b" is 40. As shown in cytotoxicity graph 1108, the $IC_{50}$ of the given second example guanidinium functionalized polycarbonate 304 against HCC827 can be 18.5 mg/L after 48 hours of treatment. Additionally, cytotoxicity graph 1110 further regards the stereocomplex chemical composition formed from a mixture of the first example guanidinium functionalized polycarbonate 302 (e.g., wherein the PEG block has an average molecular weight of 5,000 Da, "m" is 40, and "b" is 40) and the second example guanidinium functionalized polycarbonate 304 (e.g., wherein the PEG block has an average molecular weight of 5,000 Da, "m" is 43, and "b" is 40). As shown in cytotoxicity graph 1110, the $IC_{50}$ of the given stereocomplex against HCC827 can be 13.0 mg/L after 48 hours of treatment. The $IC_{50}$ values in cytotoxicity graphs 1106, 1108, and 1110 were determined from a single experiment. FIGS. 11A and/or 11B, as compared with FIGS. 7A and/or 7B, demonstrate that longer second functional groups (e.g., longer polylactic acid blocks) can lead to the formation of more stable micelles, and thereby can inhibit interaction of the polylactic acid block and the cell membrane of the target cancer cells.

Figure 12A:
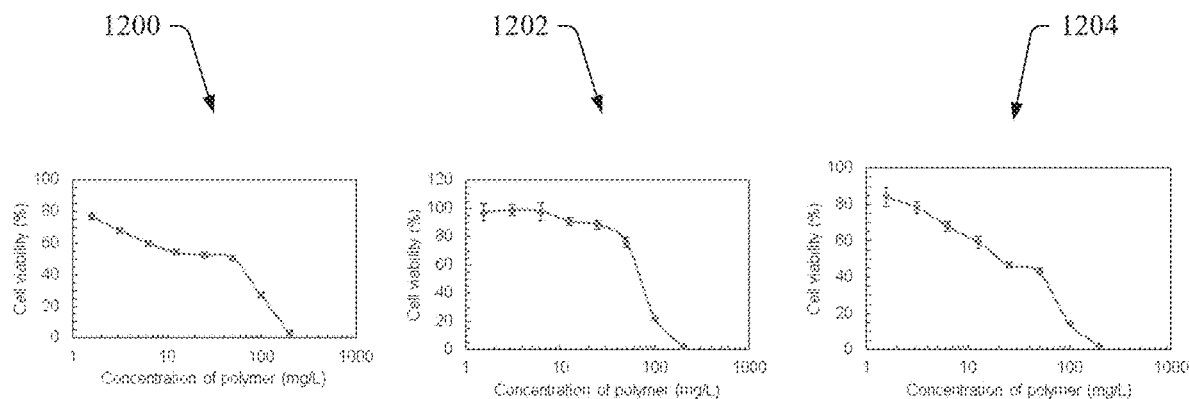
FIGS. 12A-12B illustrate diagrams of example, non-limiting cytotoxicity graphs that can depict the efficacy of anticancer activity exhibited by a chemical composition comprising a plurality of triblock polymers having a guanidinium functionalized block in accordance with one or more embodiments described herein.
Figure 12B:
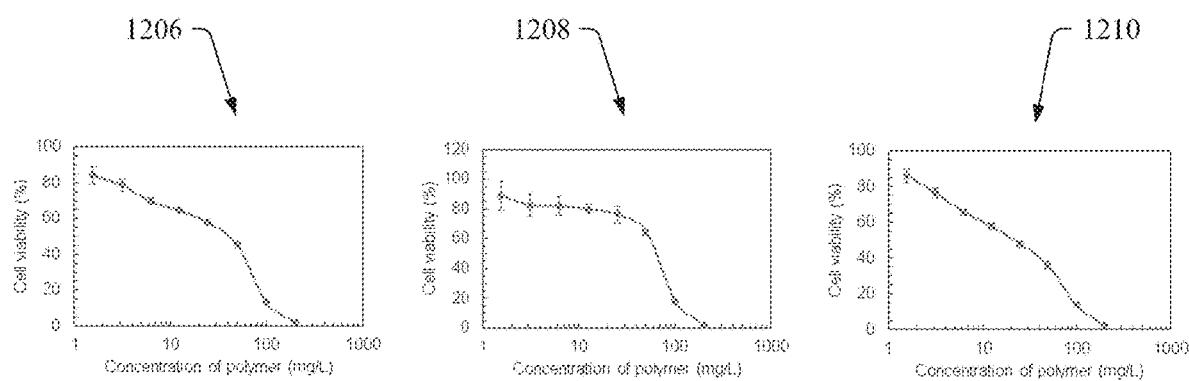

FIGS. 12A and 12B can illustrate diagrams of example, non-limiting cytotoxicity graphs regarding the guanidinium functionalized polycarbonate structures 104 against A549 human lung adenocarcinoma cell line in accordance with one or more embodiments described herein. Repetitive description of like elements employed in other embodiments described herein is omitted for sake of brevity. FIG. 12A can depict the cytotoxicity of the first example guanidinium functionalized polycarbonate 302, the second example guanidinium functionalized polycarbonate 304, and/or mixtures thereof after 24 hours of treatment against A549. FIG. 12B can depict the first example guanidinium functionalized polycarbonate 302, the second example guanidinium functionalized polycarbonate 304, and/or mixtures thereof after 48 hours of treatment against A549.

Cytotoxicity graph 1200 regards a micellar formation of the first example guanidinium functionalized polycarbonate 302; wherein the PEG block has an average molecular weight of 5,000 Da, "m" is 40, and "b" is 40. As shown in cytotoxicity graph 1200, the $IC_{50}$ of the given first example guanidinium functionalized polycarbonate 302 against A549 can be 51.8 mg/L after 24 hours of treatment. Cytotoxicity graph 1202 regards a micellar formation of the second example guanidinium functionalized polycarbonate 304; wherein the PEG block has an average molecular weight of 5,000 Da, "m" is 43, and "b" is 40. As shown in cytotoxicity graph 1202, the $IC_{50}$ of the given second example guanidinium functionalized polycarbonate 304 against A549 can be 69.8 mg/L after 24 hours of treatment. Further, cytotoxicity graph 1204 regards a stereocomplex chemical composition formed from a mixture of the first example guanidinium functionalized polycarbonate 302 (e.g., wherein the PEG block has an average molecular weight of 5,000 Da, "m" is 40, and "b" is 40) and the second example guanidinium functionalized polycarbonate 304 (e.g., wherein the PEG block has an average molecular weight of 5,000 Da, "m" is 43, and "b" is 40). As shown in cytotoxicity graph 1204, the $IC_{50}$ of the given stereocomplex against A549 can be 20.0 mg/L after 24 hours of treatment. The $IC_{50}$ values of cytotoxicity graphs 1200, 1202, and 1204 were determined from a single experiment. FIG. 12A exemplifies that the stereocomplex (e.g., a mixture of the first and second example guanidinium functionalized polycarbonate 302, 304) can exhibit stronger anticancer activity than the respective micellar formations against A549.

Cytotoxicity graph 1206 further regards the micellar formation of the first example guanidinium functionalized polycarbonate 302; wherein the PEG block has an average molecular weight of 5,000 Da, "m" is 40, and "b" is 40. As shown in cytotoxicity graph 1206, the $IC_{50}$ of the given first example guanidinium functionalized polycarbonate 302 against A549 can be 42.0 mg/L after 48 hours of treatment. Cytotoxicity graph 1208 further regards the micellar formation of the second example guanidinium functionalized polycarbonate 304; wherein the PEG block has an average molecular weight of 5,000 Da, "m" is 43, and "b" is 40. As shown in cytotoxicity graph 1208, the $IC_{50}$ of the given second example guanidinium functionalized polycarbonate 304 against A549 can be 63.4 mg/L after 48 hours of treatment. Additionally, cytotoxicity graph 1210 further regards the stereocomplex chemical composition formed from a mixture of the first example guanidinium functionalized polycarbonate 302 (e.g., wherein the PEG block has an average molecular weight of 5,000 Da, "m" is 40, and "b" is 40) and the second example guanidinium functionalized polycarbonate 304 (e.g., wherein the PEG block has an average molecular weight of 5,000 Da, "m" is 43, and "b" is 40). As shown in cytotoxicity graph 1210, the $IC_{50}$ of the given stereocomplex against A549 can be 21.4 mg/L after 48 hours of treatment. The $IC_{50}$ values of cytotoxicity graphs 1206, 1208, and 1210 were determined from a single experiment.

FIG. 13 illustrates a flow diagram of an example, non-limiting method 1300 that can facilitate administering one or more combination therapies to treat cancer cells in accordance with one or more embodiments described herein. Repetitive description of like elements employed in other embodiments described herein is omitted for sake of brevity.

At 1302, the method 1300 can comprise inhibiting a growth of cancer cells by administering a combination therapy comprising a chemical composition of guanidinium functionalized triblock polymers and quaternary ammonium functionalized triblock polymers. For example, the guanidinium functionalized triblock polymers can be characterized by the guanidinium functionalized polycarbonate structures 104 (e.g., first example guanidinium functionalized polycarbonate 302 and/or second guanidinium functionalized polycarbonate 304). Further, the quaternary ammonium functionalized triblock polymers can be characterized by the quaternary ammonium functionalized polycarbonate structures 102 (e.g., first example quaternary ammonium polycarbonate 402 and/or second quaternary ammonium polycarbonate 404). In various embodiments, the one or more guanidinium functionalized triblock polymers and quaternary ammonium functionalized triblock polymers can be mixed with one or more quaternary ammonium and guanidinium functionalized triblock polymers (e.g., characterized by quaternary ammonium and guanidinium functionalized polycarbonate structures 106, such as first and/or second example quaternary ammonium and guanidinium functionalized polycarbonates 502, 504).

In various embodiments, the chemical composition can comprise a stereocomplex of the guanidinium functionalized triblock polymers and quaternary ammonium functionalized triblock polymers. For example, the stereo complex can be characterized by the first copolymer structure 202, such as the example stereocomplex 602. Additionally, the length of the second functional group (e.g., polylactic acid block) can affect the kinetic stability of the stereocomplex.

At 1304, the method 1300 can comprise executing a lytic mechanism via the chemical composition. At 1306, the method 1300 can comprise executing a translocation mechanism via the chemical composition. As described herein, the guanidinium functionalized triblock polymers (e.g., characterized by guanidinium functionalized polycarbonate structures 104) can exhibit anticancer activity via the translocation mechanism, and the quaternary ammonium functionalized triblock polymers (e.g., characterized by quaternary ammonium polycarbonate structures 102) can exhibit anticancer activity via the lytic mechanism. Chemical compositions comprising both the guanidinium functionalized triblock polymers and quaternary ammonium functionalized triblock polymers can utilize both distinct mechanism, lytic and translocation, to enhance the respective anticancer activities. For example, at least FIGS. 10A and/or 10B depict the synergistic effect that can be achieved by stereocomplexes of the chemical composition utilized in method 1300.

Figure 14:
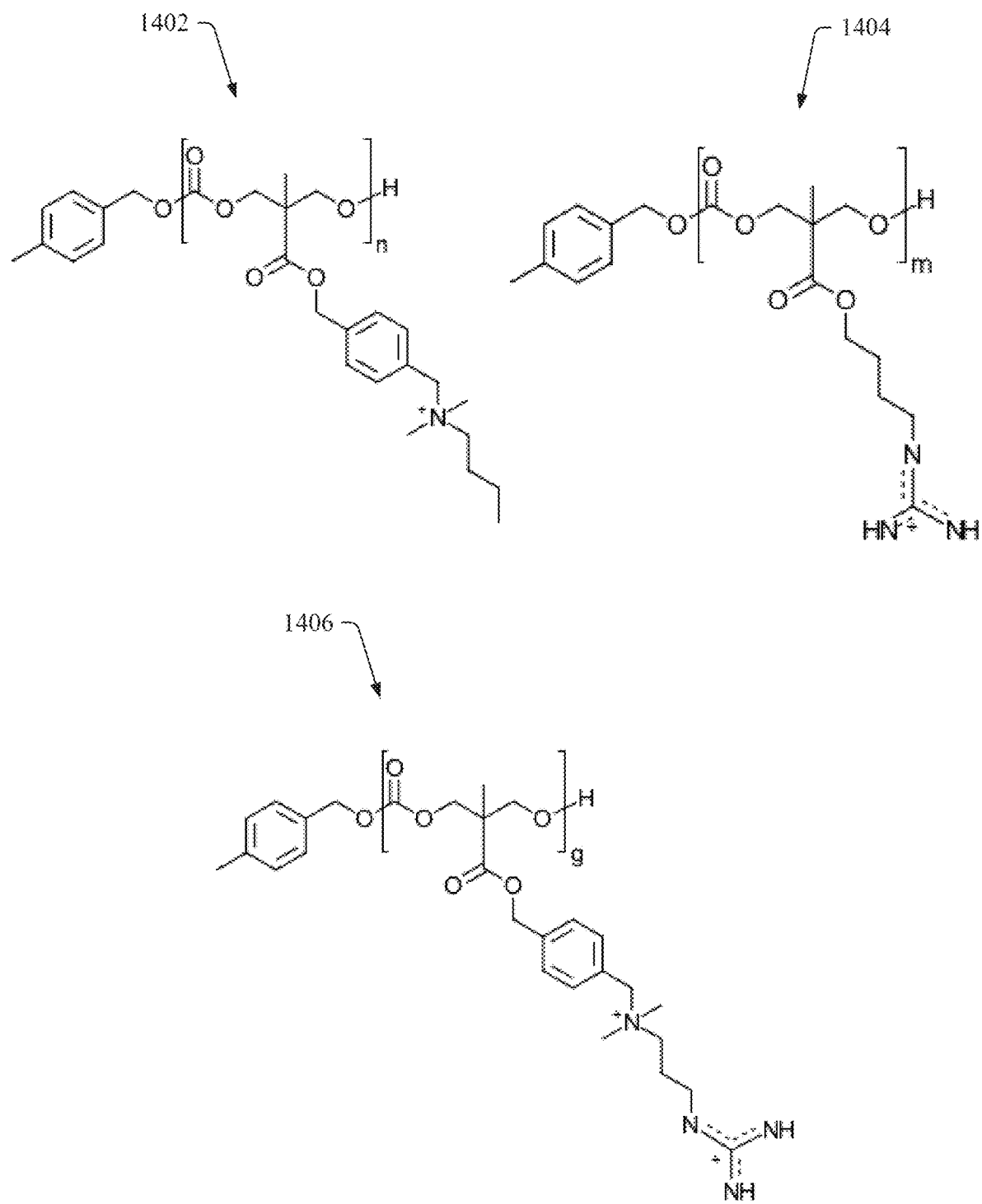
FIG. 14 illustrates a diagram of example, non-limiting antimicrobial polymers that can be utilized in one or more combination therapies to inhibit the growth of one or more microbes in accordance with one or more embodiments described herein.

FIG. 14 illustrates a diagram of example, non-limiting antimicrobial polymers that can further exemplify the chemical structures of FIG. 1 and/or can be utilized in one or more combination therapies targeting one or more microbes in accordance with one or more embodiments described herein. Repetitive description of like elements employed in other embodiments described herein is omitted for sake of brevity. As shown in FIG. 14, the exemplary antimicrobial polymers can include an example quaternary ammonium functionalized antimicrobial polymer 1402, an example guanidinium functionalized antimicrobial polymer 1404, and/or an example quaternary ammonium and guanidinium functionalized antimicrobial polymer 1406.

The example antimicrobial polymers can comprise one or more benzyl aryl groups as the one or more first functional groups. Further, the example antimicrobial polymers can comprise hydrogen as the one or more second functional groups. The example quaternary ammonium functionalized antimicrobial polymer 1402 can comprise a benzyl aryl linkage group and/or a butyl fifth functional group. The example guanidinium functionalized antimicrobial polymer 1404 can comprise butyl linkage group. Also, the example quaternary ammonium and guanidinium functionalized antimicrobial polymer 1406 can comprise a benzyl aryl linkage group and a propyl fifth functional group.

In various embodiments, the example quaternary ammonium functionalized antimicrobial polymer 1402 can exhibit antimicrobial activity via a lytic mechanism. The example guanidinium functionalized antimicrobial polymer 1404 can exhibit antimicrobial activity via a translocation mechanism. Also, the example quaternary ammonium and guanidinium functionalized antimicrobial polymer 1406 can exhibit antimicrobial activity via a lytic mechanism and/or a translocation mechanism.

Additionally, Table 1 below can demonstrate the anticancer activity of example quaternary ammonium functionalized antimicrobial polymer 1402, wherein "n" is 20 ("pQuat_20"); example guanidinium functionalized antimicrobial polymer 1404, wherein "m" is 20 ("pBut_20"); and combinations thereof. Table 1 can regard the anticancer activity against HepG2 cancer cells with an incubation time of 24 hours. For the combination therapies, the cancer cells were treated with pQuat_20 for 4 hours followed by treatment with pBut_20 for 20 hours.

TABLE 1

| Treatment Composition | $IC_{50}$ (µg/mL) |
|---|---|
| pQuat_20 | 56.5 |
| pBut_20 | 69.7 |
| Mixture | 45.0 |

Figure 15:
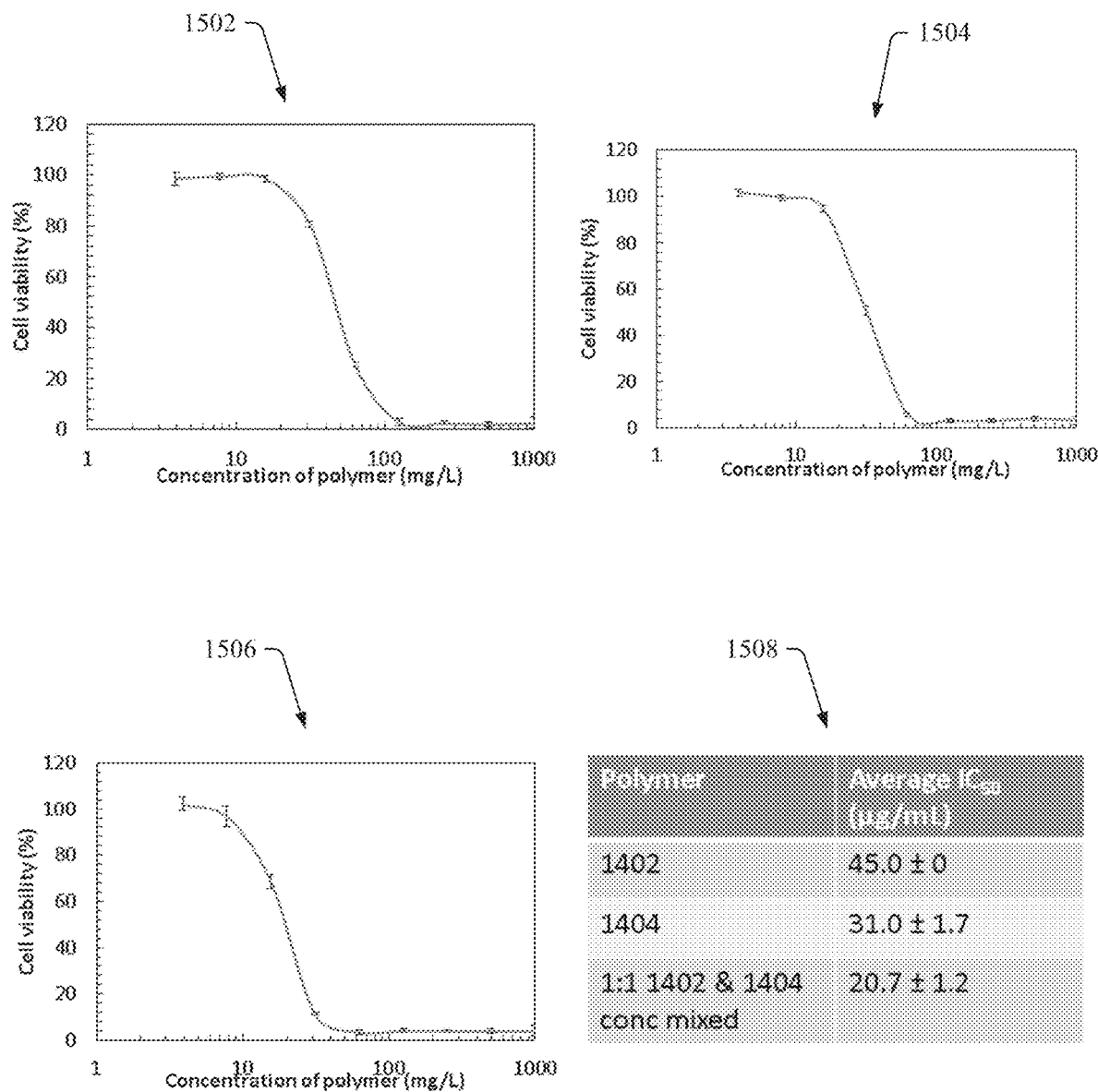
FIG. 15 illustrates a diagram of example, non-limiting cytotoxicity graphs that can depict the efficacy of anticancer activity exhibited by one or more functionalized polycarbonate compounds in accordance with one or more embodiments described herein.

FIG. 15 illustrates a diagram of example, non-limiting cytotoxicity graphs regarding the anticancer activity of the one or more example quaternary ammonium functionalized antimicrobial polymers 1402, example guanidinium functionalized antimicrobial polymers 1404, and/or combinations thereof against A549 cancer cell in accordance with one or more embodiments described herein.

Cytotoxicity graph 1502 regards the anticancer activity of example quaternary ammonium functionalized antimicrobial polymers 1402. As shown in cytotoxicity graph 1502, the average $IC_{50}$ of example quaternary ammonium functionalized antimicrobial polymer 1402 against A549 cells can be 45.0±0 µg/mL after 48 hours of treatment. Cytotoxicity graph 1504 regards the anticancer activity of example guanidinium functionalized antimicrobial polymers 1404. As shown in cytotoxicity graph 1504, the average $IC_{50}$ of example guanidinium functionalized antimicrobial polymers 1404 against A549 cells can be 31.0±1.7 µg/mL after 48 hours of treatment. Additionally, cytotoxicity graph 1506 regards the anticancer activity of a chemical composition formed from an equiconcentration mixture of example quaternary ammonium functionalized antimicrobial polymers 1402 and example guanidinium functionalized antimicrobial polymers 1404. As shown in cytotoxicity graph 1506, the average $IC_{50}$ of the given mixture can be 20.7±1.2 µg/mL after 48 hours of treatment. The average $IC_{50}$ values in cytotoxicity graphs 1502, 1504, and/or 1506 were determined from three individual sets of experiments. Cytotoxicity graph 1506 exemplifies that the given mixture can exhibit stronger anticancer activity than the respective polymers against A549 cells. Further, the cytotoxicity table 1508 can characterize the anticancer activity of the respective antimicrobial polymers and/or mixtures thereof against the A549 cancer cells.

Regarding the cytotoxicity graphs of FIG. 15, the cytotoxicity of the polymers and/or combination therapy was examined through one or more Alamar Blue assays. The target cells were seeded onto 96 well plates at a density of $5\times10^3$ cells per well and incubated overnight in 100 microliters (µL) of medium at 37° C., 5% $CO_2$. The solutions of the given polymers and/or combination therapy were then diluted in media to obtain various concentrations. The medium in each well was then replaced with the sample solution at 100 µL and the plates were incubated 37° C., 5% $CO_2$ for 24 hours or 48 hours. Six replicates were tested for each concentration. Medium was as the positive control. At the end of incubation, the sample solution was replaced with 90 µL of fresh medium and 10 µL of Alamar Blue solution (10% v/v). The plates were then maintained at 37° C., 5% $CO_2$ for 2 hours. After 2 hours, the fluorescence of Resazurin compound was measured with peak excitation of 560 nm and peak emission of 590 nm using a microplate reader. Cell viability was expressed as a percentage of fluorescence of the control cells with the subtraction of background fluorescence obtained from negative controls from both sample and positive controls.

Figure 16:
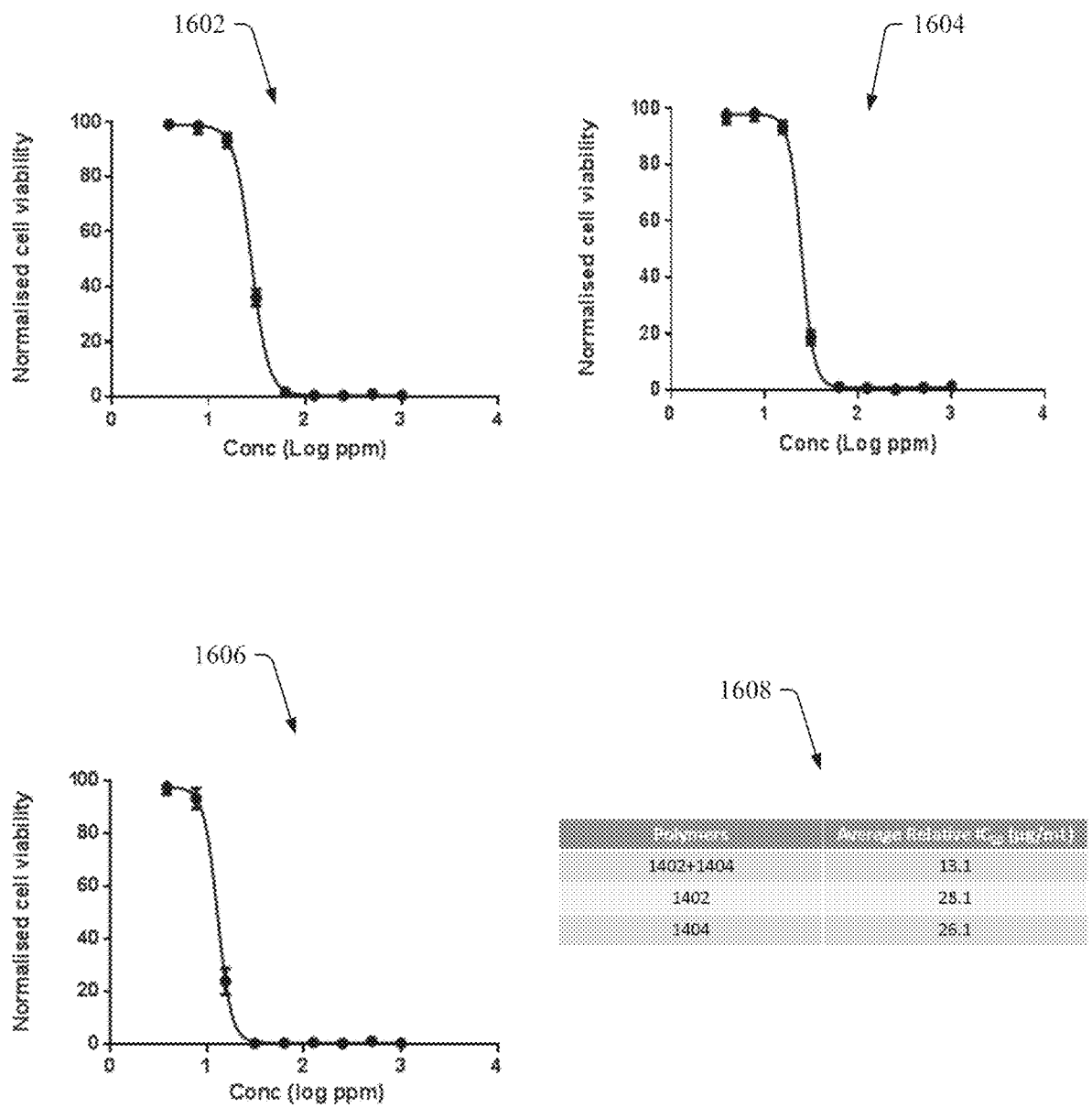
FIG. 16 illustrates a diagram of example, non-limiting cytotoxicity graphs that can depict the efficacy of anticancer activity exhibited by one or more functionalized polycarbonate compounds in accordance with one or more embodiments described herein.

FIG. 16 illustrates a diagram of example, non-limiting cytotoxicity graphs regarding the anticancer activity of the one or more example quaternary ammonium functionalized antimicrobial polymers 1402, example guanidinium functionalized antimicrobial polymers 1404, and/or combinations thereof against HepG2 cancer cell in accordance with one or more embodiments described herein.

Cytotoxicity graph 1602 regards the anticancer activity of example quaternary ammonium functionalized antimicrobial polymers 1402 against HepG2 cells. As shown in cytotoxicity graph 1602, the average $IC_{50}$ of example quaternary ammonium functionalized antimicrobial polymers 1402 against HepG2 cells can be 28.1 µg/mL after 48 hours of treatment. Cytotoxicity graph 1604 regards the anticancer activity of example guanidinium functionalized antimicrobial polymers 1404. As shown in cytotoxicity graph 1604, the average $IC_{50}$ of example guanidinium functionalized antimicrobial polymers 1404 against HepG2 cells can be 26.1 µg/mL after 48 hours of treatment. Additionally, cytotoxicity graph 1606 regards the anticancer activity of a chemical composition formed from an equiconcentration mixture of example quaternary ammonium functionalized antimicrobial polymers 1402 and example guanidinium functionalized antimicrobial polymers 1404. As shown in cytotoxicity graph 1606, the average $IC_{50}$ of the given mixture can be 13.1 µg/mL after 48 hours of treatment. The average $IC_{50}$ values in cytotoxicity graphs 1602, 1604, and 1606 were determined from one experiment. Cytotoxicity graph 1606 exemplifies that the given mixture can exhibit stronger anticancer activity than the respective polymers against HepG2 cells. Further, the cytotoxicity table 1608 can characterize the anticancer activity of the respective antimicrobial polymers and/or mixtures thereof against the HepG2 cancer cells.

Regarding the cytotoxicity graphs of FIG. 16, the cytotoxicity of the polymers and/or combination therapy was examined through one or more Alamar Blue assays. The target cells were seeded onto 96 well plates at a density of $5\times10^3$ cells per well and incubated overnight in 100 microliters (µL) of medium at 37° C., 5% $CO_2$. The solutions of the given polymers and/or combination therapy were then diluted in media to obtain various concentrations. The medium in each well was then replaced with the sample solution at 100 μL and the plates were incubated 37° C., 5% $CO_2$ for 24 hours or 48 hours. Six replicates were tested for each concentration. Medium was as the positive control. At the end of incubation, the sample solution was replaced with 90 μL of fresh medium and 10 μL of Alamar Blue solution (10% v/v). The plates were then maintained at 37° C., 5% $CO_2$ for 2 hours. After 2 hours, the fluorescence of Resazurin compound was measured with peak excitation of 560 nm and peak emission of 590 nm using a microplate reader. Cell viability was expressed as a percentage of fluorescence of the control cells with the subtraction of background fluorescence obtained from negative controls from both sample and positive controls.

Figure 17:
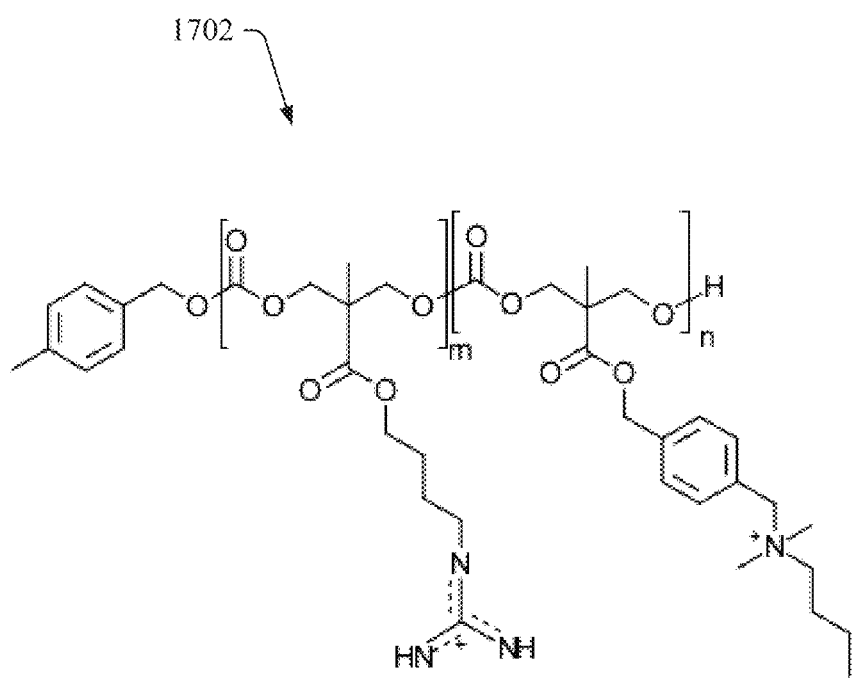
FIG. 17 illustrates a diagram of an example, non-limiting antimicrobial copolymer that can be utilized in one or more combination therapies to inhibit the growth of one or more microbes in accordance with one or more embodiments described herein.

FIG. 17 illustrates a diagram of example, non-limiting an antimicrobial copolymer 1702 that can exemplify the second copolymer structure 204 and/or can be utilized in one or more combination therapies targeting one or more microbes in accordance with one or more embodiments described herein. Repetitive description of like elements employed in other embodiments described herein is omitted for sake of brevity. As shown in FIG. 17, the example antimicrobial copolymer 1702 can comprise: a benzyl aryl first functional group, a hydrogen second functional group, one or more butyl linkage groups bonded to the one or more guanidinium functional groups, one or more benzyl aryl groups bonded to the one or more quaternary ammonium functional groups, and/or a butyl fifth functional group. Additionally, the one or more guanidinium functionalized polycarbonate blocks can be directly bonded to the one or more quaternary ammonium functionalized polycarbonate blocks. In various embodiments, the example antimicrobial copolymer 1702 can be a block copolymer or a random block copolymer.

Figures 18A, 18B:
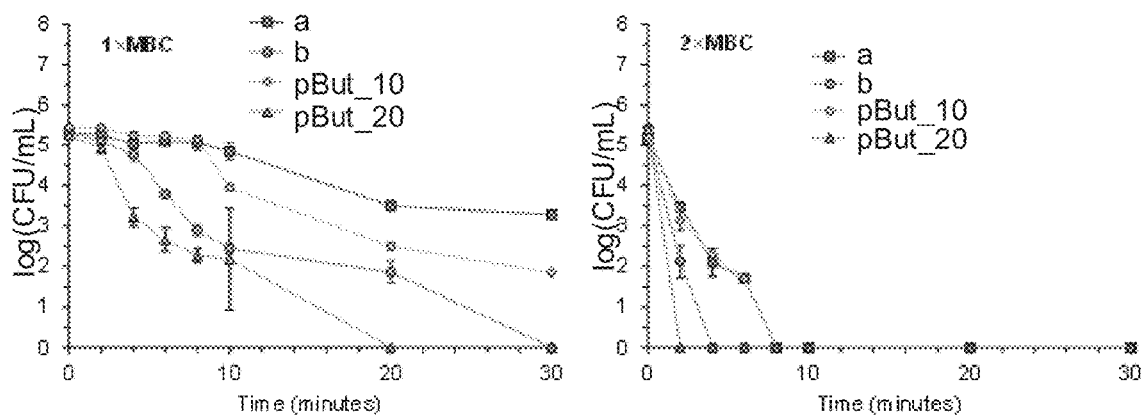
FIGS. 18A-18B illustrate diagrams of example, non-limiting tables and/or graphs that can demonstrate the antimicrobial activity of one or more antimicrobial polymers and/or combination therapies in accordance with one or more embodiments described herein.

FIGS. 18A and/or 18B illustrates diagrams of example non-limiting tables and graphs that can demonstrate the antimicrobial activity of the example antimicrobial polymers in accordance with one or more embodiments described herein. Repetitive description of like elements employed in other embodiments described herein is omitted for sake of brevity. As shown in FIGS. 18A and/or 18B: "pQuat_20" can indicate the example quaternary ammonium functionalized antimicrobial polymer 1402, wherein "n" is 20; "pBut_10" can indicate the example guanidinium functionalized antimicrobial polymer 1404, wherein "m" is 10; "pBut_20" can indicate the example guanidinium functionalized antimicrobial polymer 1404, wherein "m" is 20; "a" can represent a block polymer configuration of the example antimicrobial copolymer 1702, wherein "n" and "m" are both 10; and "b" can represent a random block polymer configuration of the example antimicrobial copolymer 1702, wherein "n" and "m" are both 10. Additionally, the "MBC" can stand for the minimum bactericidal concentration, and "CFU/mL" can stand for colony forming unit per milliliter. The graphs depicted in FIG. 18B regard the example antimicrobial polymers against P. aeruginosa at corresponding 1xMBC and 2xMBC.

As shown in FIGS. 18A and/or 18B, the block copolymer ("a") and random block ("b") copolymer configurations of the example antimicrobial copolymer 1702 can have comparable antimicrobial potency with similar MIC and MBC values against the bacteria and fungi as compared to the example guanidinium functionalized antimicrobial polymer 1404, although there were only 10 guanidinium groups in the example antimicrobial copolymer 1702. The random block ("b") copolymer configuration terminated P. aeruginosa more rapidly than the example guanidinium functionalized antimicrobial polymer 1404 ("pBut_10") at both 1xMBC and 2xMBC, indicating that the presence of quaternary ammonium enhanced killing efficiency of the example guanidinium functionalized antimicrobial polymer 1404 ("pBut_10"). The quaternary ammonium groups can enhance interaction with the bacterial membrane and strengthen antimicrobial activity of the example antimicrobial copolymer 1702.

Figure 19A:
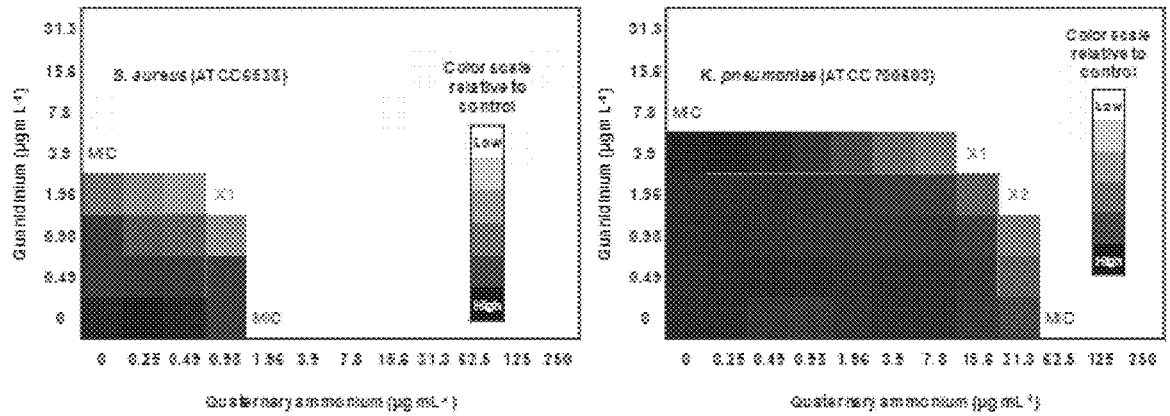
FIGS. 19A-19C illustrate diagrams of example, non-limiting checkerboard assays that can depict the efficacy of antimicrobial activity exhibited by a chemical composition comprising a quaternary ammonium functionalized polycarbonate and a guanidinium functionalized polycarbonate in accordance with one or more embodiments described herein.
Figure 19B:
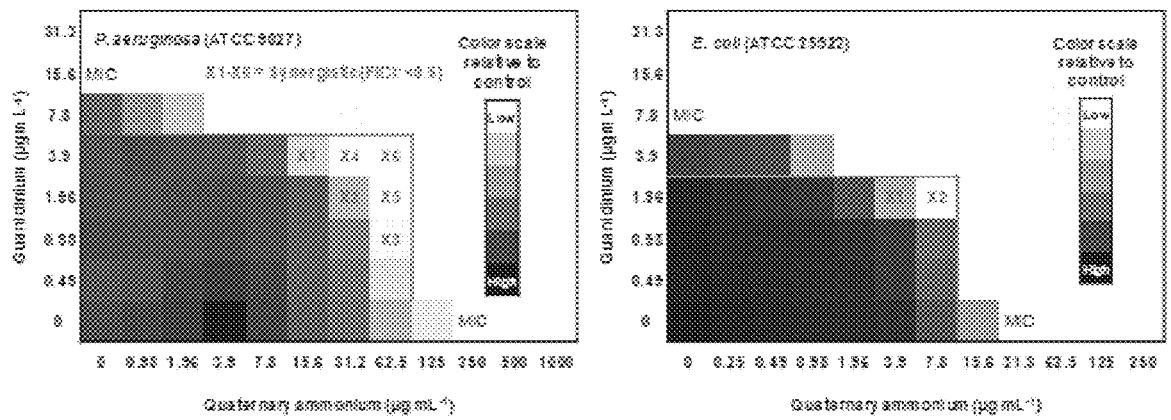
Figure 19C:
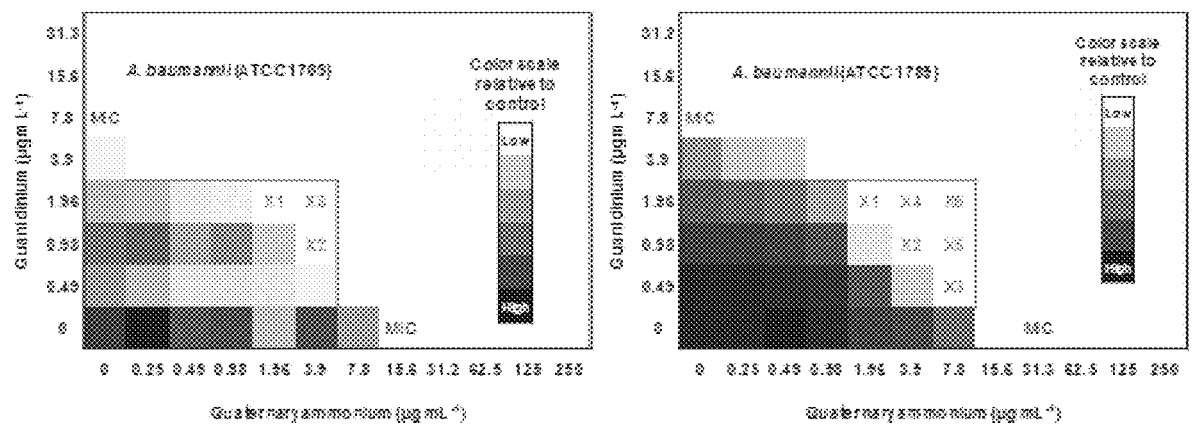

FIGS. 19A-19C illustrate diagrams of example, non-limiting checkerboard assays regarding the antimicrobial effect of a combination therapies that can include antimicrobial polymers characterized by at least the quaternary ammonium functionalized polycarbonate structure 102 and/or the guanidinium functionalized polycarbonate structure 104. Repetitive description of like elements employed in other embodiments described herein is omitted for sake of brevity. As shown in FIGS. 19A-19C "X" can represent respective concentrations of the antimicrobial polymers.

FIG. 19A depicts checkerboard assay of a sample combination therapy comprising the example quaternary ammonium functionalized antimicrobial polymer 1402 (e.g., wherein "n" is 20) and the example guanidinium functionalized antimicrobial polymer 1404 (e.g., wherein "m" is 20) against S. aureus and K. pneumoniae. The sample combination therapy can exhibit an additive effect between the two antimicrobial polymers observed at concentrations of ×1-×2 (e.g., 0.5<FICI<1.0, wherein "FICI" is the fractional inhibitory concentration index). FIG. 19B depicts checkerboard assays of the sample combination therapy against P. aeruginosa and E. coli. The sample combination therapy can exhibit a synergistic effect observed between the two antimicrobial polymers at concentrations of ×1-×6 and ×1-×2, respectively (e.g., FICI<0.5). FIG. 19C depicts checkerboard assays of the sample combination therapy against therapeutic-susceptible A. baumannii and therapeutic-resistant A. baumannii. The combination therapy can exhibit a synergistic effect observed between the two antimicrobial polymers at concentrations of ×1-×3 and ×1-×6, respectively (e.g., FICI<0.5).

As exemplified by FIG. 19A, the combination of guanidinium functionalized polycarbonate structures 104 and quaternary ammonium functionalized polycarbonate structures 102, having two distinctive antimicrobial mechanisms (e.g., lytic mechanisms and translocation mechanisms), can exert additive effects against bacteria such as S. aureus and K. pneumoniae. Additionally, as exemplified in FIG. 19B, the combination of guanidinium functionalized polycarbonate structures 104 and quaternary ammonium functionalized polycarbonate structures 102 can demonstrate a strong synergistic effect against bacteria such as P. aeruginosa and E. coli.

For instance, at ½×MIC of the example guanidinium functionalized antimicrobial polymer 1404 (e.g., wherein "m" is 20) (e.g., 7.8 micrograms per milliliter (μg/mL)), the MIC of the example quaternary ammonium functionalized antimicrobial polymer 1402 (e.g., wherein "n" is 20) can be reduced from 250 to 3.9 μg/mL against *P. aeruginosa* (e.g., 63 folds reduction). Also, at ¼×MIC of the example guanidinium functionalized antimicrobial polymer 1404 (e.g., wherein "n" is 20) (e.g., 3.9 μg/mL), MIC of the example quaternary ammonium functionalized antimicrobial polymer 1402 (e.g., wherein "n" is 20) can be reduced from 250 to 31.3 μg/mL (e.g., 7 folds reduction). In the case of *E. coli*, at ¼×MIC of the example guanidinium functionalized antimicrobial polymer 1404 (e.g., wherein "n" is 20) (e.g., 1.96 μg/mL), MIC of the example quaternary ammonium functionalized antimicrobial polymer 1402 (e.g., wherein "n" is 20) can be reduced from 31.3 to 7.8 μg/mL against *P. aeruginosa* (e.g., 3 folds reduction). The presence of the guanidinium functionalized polycarbonate structures 104 can significantly enhanced antimicrobial activity of the quaternary ammonium functionalized polycarbonate structures 102.

Moreover, a strong synergy can also be observed for combinations of the guanidinium functionalized polycarbonate structures 104 and quaternary ammonium functionalized polycarbonate structures 102 against therapeutic-susceptible bacteria, such as *A. baumannii*, and/or therapeutic-resistant bacteria, such as *A. baumannii*. For example, in the presence of ¼×MIC of the example guanidinium functionalized antimicrobial polymer 1404 (e.g., wherein "n" is 20) (e.g., 1.96 μg/mL), the MIC of the example quaternary ammonium functionalized antimicrobial polymer 1402 (e.g., wherein "n" is 20) can be decreased from 15.6 to 1.96 μg/mL against both therapeutic-susceptible and therapeutic-resistant *A. baumannii* (e.g., about 7 folds reduction).

FIGS. 19A-19C can demonstrate that a combination therapy of the quaternary ammonium functionalized polycarbonate structures 102 and the guanidinium functionalized polycarbonate structures 104 can achieve a synergistic effect that leverages both lytic mechanisms and translocation mechanisms in antimicrobial activity. In various embodiments, the translocation mechanism exhibited by the one or more guanidinium functionalized polycarbonate structures 104 can precipitate one or more cytosolic members (e.g., proteins, enzymes, and/or genes) in the target microbe that could otherwise impede the lytic mechanism of the one or more quaternary ammonium functionalized polycarbonate structures 102. Thereby, the combination of the quaternary ammonium functionalized polycarbonate structures 102 and the guanidinium functionalized polycarbonate structures 104 can enhance antimicrobial activity (e.g., respective of the antimicrobial activity of the polymers respectively) against microbes (e.g., bacteria), such as therapeutic-resistant microbes (e.g., antimicrobial-resistant bacteria).

Figure 20:
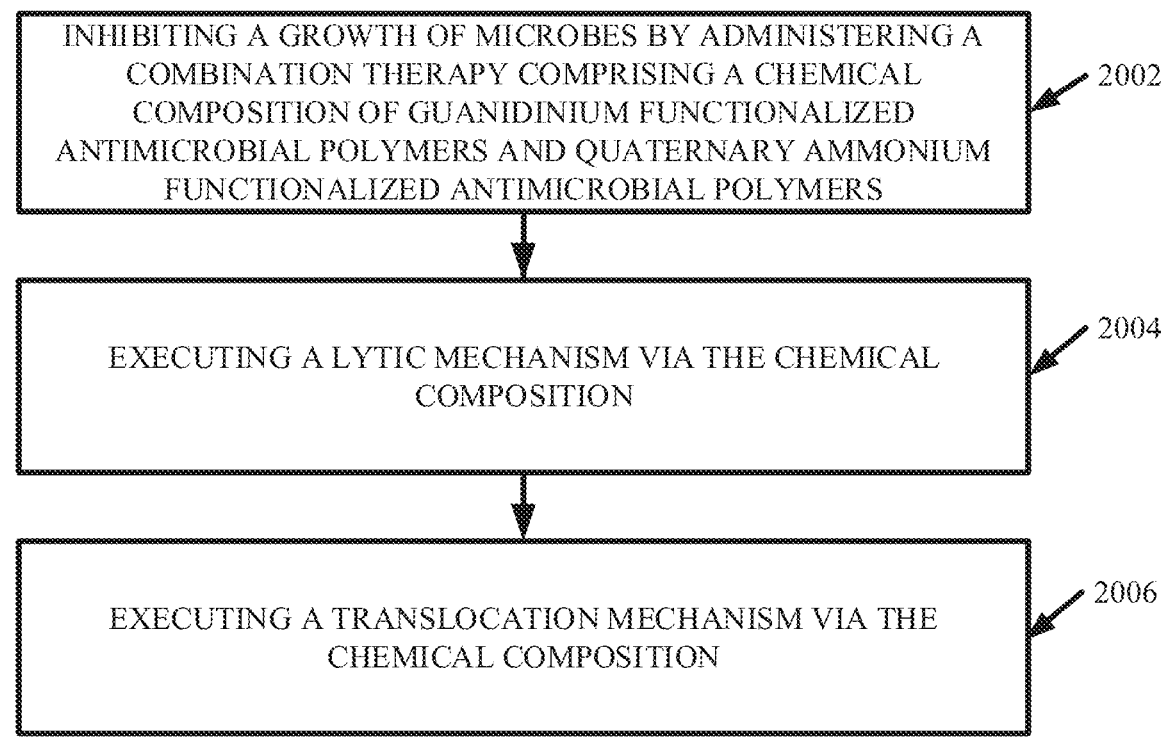
FIG. 20 illustrate a flow diagram of an example, non-limiting method that can facilitate performing a combination therapy utilizing one or more quaternary ammonium functionalized polycarbonates and/or guanidinium functionalized polycarbonates to inhibit the growth of one or more microbes in accordance with one or more embodiments describe herein.

FIG. 20 illustrates a flow diagram of an example, non-limiting method 2000 that can facilitate administering one or more combination therapies to inhibit microbe growth in accordance with one or more embodiments described herein. Repetitive description of like elements employed in other embodiments described herein is omitted for sake of brevity.

At 2002, the method 2000 can comprise inhibiting a growth of one or more microbes by administering a combination therapy comprising a chemical composition of guanidinium functionalized antimicrobial polymers (e.g., characterized by guanidinium functionalized polycarbonate structures 104) and quaternary ammonium functionalized antimicrobial polymers (e.g., characterized by quaternary ammonium functionalized polycarbonate structures 102). For example, the guanidinium functionalized antimicrobial polymers can be exemplified by the example guanidinium functionalized antimicrobial polymers 1404. Also, the quaternary ammonium functionalized antimicrobial polymers can be exemplified by example quaternary ammonium functionalized antimicrobial polymers 1402. In various embodiments, the one or more guanidinium functionalized antimicrobial polymers and quaternary ammonium functionalized antimicrobial polymers can be mixed with one or more quaternary ammonium and guanidinium functionalized antimicrobial polymers (e.g., characterized by quaternary ammonium and guanidinium functionalized polycarbonate structures 106).

At 2004, the method 2000 can comprise executing a lytic mechanism via the chemical composition. At 2006, the method 2000 can comprise executing a translocation mechanism via the chemical composition. As described herein, the guanidinium functionalized antimicrobial polymers (e.g., exemplified by example guanidinium functionalized antimicrobial polymers 1404 and/or antimicrobial copolymer 1702) can exhibit antimicrobial activity via the translocation mechanism. Further, the quaternary ammonium functionalized antimicrobial polymers (e.g., exemplified by the example quaternary ammonium functionalized antimicrobial polymers 102 and/or antimicrobial copolymer 1702) can exhibit antimicrobial activity via the lytic mechanism. Chemical compositions comprising both the guanidinium functionalized antimicrobial polymers and quaternary ammonium functionalized antimicrobial polymers can utilize both distinct mechanism, lytic and translocation, to enhance the respective antimicrobial activities. For example, at least FIGS. 19A-19C depict the synergistic effect that can be achieved by the chemical composition utilized in method 2000.

In various embodiments, the one or more antimicrobial polymers characterized by the chemical structures of FIG. 1 and/or exemplified in FIG. 14 can further be utilized in one or more combination therapies with one or more chemotherapeutic agents to treat cancer cells. For example, the one or more antimicrobial polymers can have a synergistic effect with the one or more chemotherapeutic agents to enhance the anticancer activity of the chemotherapeutic agents. Example chemotherapeutic agents that can be utilized in the combination therapy with the antimicrobial polymers can include, but are not limited to: doxorubicin, paclitaxel, a combination thereof, and/or the like. Advantageously, combination therapies comprising chemical compositions of chemotherapeutic agents mixed with antimicrobial polymers (e.g., characterized by quaternary ammonium functionalize polycarbonate structures 102, guanidinium functionalized polycarbonate structures 104, and/or quaternary ammonium and guanidinium functionalized polycarbonate structures 106) can treat therapeutic-resistant cancer strains while reducing the $IC_{50}$ value and mitigating toxicity.

For example, Tables 2 and 3 below demonstrates the anticancer activity of doxorubicin ("DOX"); example quaternary ammonium functionalized antimicrobial polymer 1402, wherein "n" is 20 ("pQuat_20"); example guanidinium functionalized antimicrobial polymer 1404, wherein "m" is 20 ("pBut_20"); and combinations thereof. Further, Table 2 regards anticancer activity against therapeutic-susceptible MCF7 cancer cells with an incubation time of 48 hours. For the combination therapies, the cancer cells were treated with the antimicrobial polymer for 4 hours followed by treatment with doxorubicin for 44 hours. Also, Table 3 regards anticancer activity against therapeutic-resistant MCF7 cancer cells with an incubation time of 48 hours. For the combination therapies, the cancer cells were treated with the antimicrobial polymer for 4 hours followed by treatment with doxorubicin for 44 hours.

TABLE 2

| Treatment Composition | Absolute $IC_{50}$ (μg/mL) |
| --- | --- |
| DOX | 0.054 |
| pQuat_20 | 18.5 |
| pBut_20 | 24.1 |
| DOX + 0.5 × $IC_{50}$pQuat_20 | 0.88 |
| DOX + 0.5 × $IC_{50}$pBut_20 | 0.20 |

TABLE 3

| Treatment Composition | Absolute $IC_{50}$ (μg/mL) |
| --- | --- |
| DOX | 375 |
| pQuat_20 | 45.0 |
| pBut_20 | 23.2 |
| DOX + 0.5 × $IC_{50}$pQuat_20 | 11.2 |
| DOX + 0.5 × $IC_{50}$pBut_20 | 37.4 |

As shown in Tables 2 and/or 3, the presence of pQuat_20 or pBut_20 at ½×$IC_{50}$ did not sensitize therapeutic-susceptible human breast cancer MCF7 cells; while their combination with DOX at their corresponding ½×$IC_{50}$ reduced $IC_{50}$ of DOX by about 33 folds and 9 folds for pQuat_20 and pBut_20, respectively, against therapeutic-resistant cancer cells. The membrane disruptive polymer pQuat_20 can provide strong enhancement as it can increase cellular uptake of DOX by overcoming the efflux pump effect in therapeutic-resistant cancer cells. Thereby demonstrating that the antimicrobial polymers described herein can be used as adjuvants to reduce anticancer therapeutic-resistance phenotype.

Figure 21:
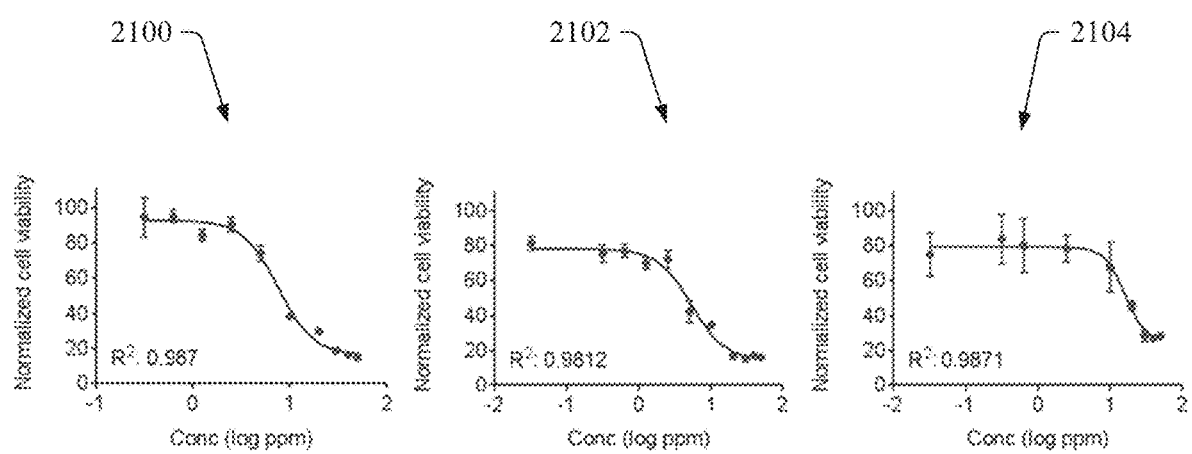
FIG. 21 illustrates a diagram of example, non-limiting graphs that can demonstrate the efficacy of anticancer activity by a chemical composition comprising one or more chemotherapeutic agents and macromolecular chemotherapeutic polycarbonate polymers in accordance with one or more embodiments described herein.

FIG. 21 illustrates a diagram of example, non-limiting cytotoxicity graphs regarding one or more combination therapies utilizing a chemical composition that combines doxorubicin with antimicrobial polymers (e.g., quaternary ammonium functionalized polycarbonate structures 102, guanidinium functionalized polycarbonate structures 104, and/or quaternary ammonium and guanidinium functionalized polycarbonate structure 106) to treat a BT474 cell line in accordance with one or more embodiments described herein. Repetitive description of like elements employed in other embodiments described herein is omitted for sake of brevity.

Cytotoxicity graph 2100 regards treating BT474 solely with doxorubicin. An absolute $IC_{50}$ value of doxorubicin in treating BT474 is 8.42 μg/mL. Cytotoxicity graph 2102 regards treating BT474 with a combination therapy of doxorubicin with 0.5 $IC_{50}$ of the example quaternary ammonium functionalized antimicrobial polymer 1402 (e.g., wherein "n" equals 21). An absolute $IC_{50}$ value of a chemical composition comprising doxorubicin with 0.5 $IC_{50}$ of the example quaternary ammonium functionalized antimicrobial polymer 1402 in treating BT474 is 4.71 μg/mL. Cytotoxicity graph 2104 regards treating BT474 with a combination therapy of doxorubicin with 0.5 $IC_{50}$ of the example guanidinium functionalized antimicrobial polymer 1404 (e.g., wherein "m" equals 20). An absolute $IC_{50}$ value of a chemical composition comprising doxorubicin with 0.5 $IC_{50}$ of the example guanidinium functionalized antimicrobial polymer 1404 in treating BT474 is 16.9 μg/mL. Thus, FIG. 21 demonstrates that the presence of the quaternary ammonium functionalized polycarbonate structures 102 (e.g., such as example quaternary ammonium functionalized antimicrobial polymer 1402) can enhance the anticancer activity of doxorubicin.

Figure 22:
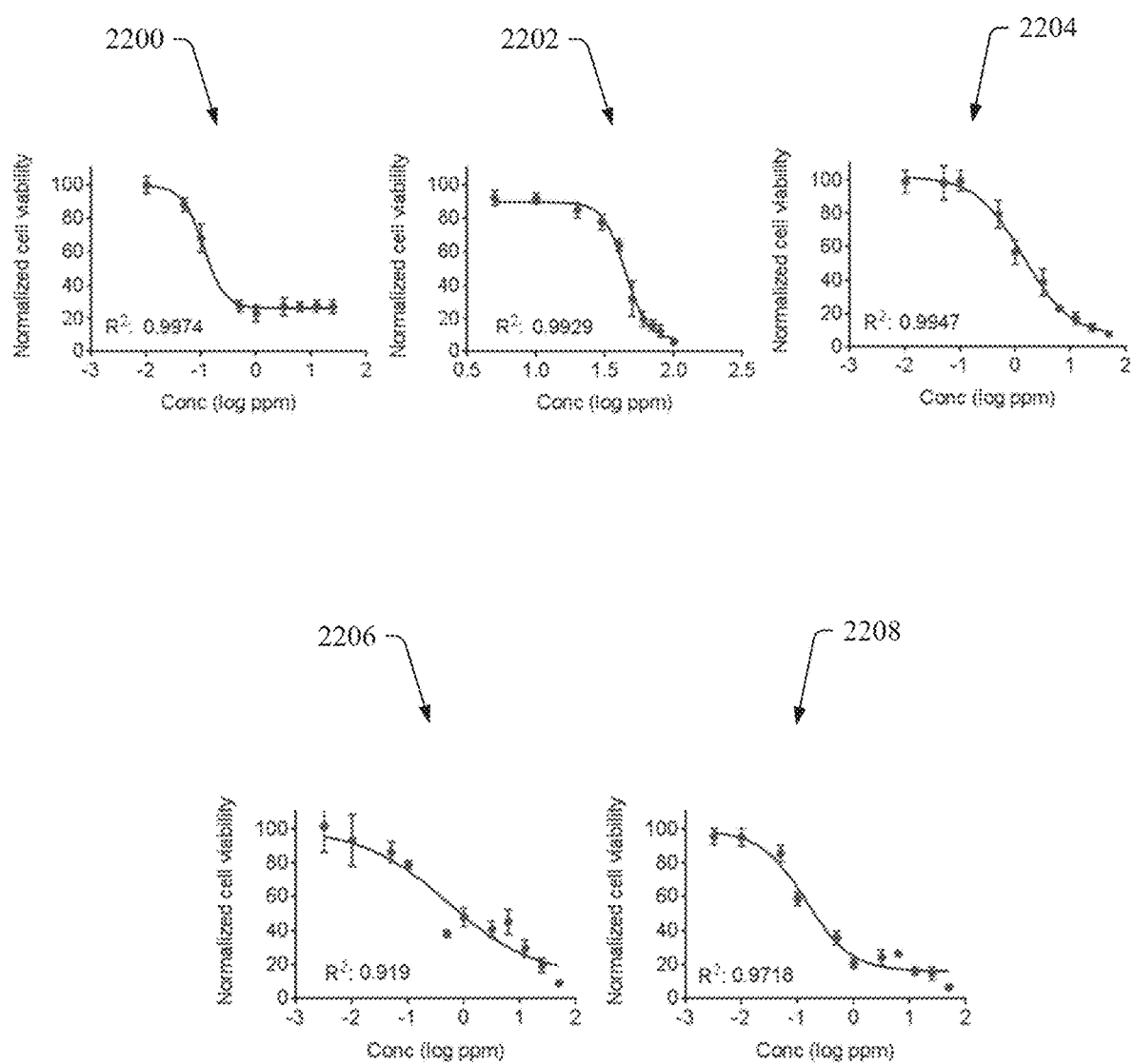
FIG. 22 illustrates a diagram of example, non-limiting graphs that can demonstrate the efficacy of anticancer activity by a chemical composition comprising one or more chemotherapeutic agents and macromolecular chemotherapeutic polycarbonate polymers in accordance with one or more embodiments described herein.

FIG. 22 illustrates a diagram of example, non-limiting cytotoxicity graphs regarding one or more combination therapies utilizing a chemical composition that combines doxorubicin with antimicrobial polymers (e.g., quaternary ammonium functionalized polycarbonate structures 102, guanidinium functionalized polycarbonate structures 104, and/or quaternary ammonium and guanidinium functionalized polycarbonate structure 106) to treat a therapeutic-susceptible MCF7 cell line in accordance with one or more embodiments described herein. Repetitive description of like elements employed in other embodiments described herein is omitted for sake of brevity.

Cytotoxicity graph 2200 regards treating MCF7 solely with doxorubicin. An absolute $IC_{50}$ value of doxorubicin in treating MCF7 is 0.15 μg/mL. Cytotoxicity graph 2202 regards treating MCF7 solely with the example quaternary ammonium functionalized antimicrobial polymer 1402 (e.g., wherein "n" equals 21). An absolute $IC_{50}$ value of the example quaternary ammonium functionalized antimicrobial polymer 1402 in treating MCF7 is 43.7 μg/mL. Cytotoxicity graph 2204 regards treating MCF7 solely with the example guanidinium functionalized antimicrobial polymer 1404 (e.g., wherein "m" equals 20). An absolute $IC_{50}$ value of example guanidinium functionalized antimicrobial polymer 1404 in treating MCF7 is 1.67 μg/mL. Cytotoxicity graph 2206 regards treating MCF7 with a combination therapy of doxorubicin with 0.5 $IC_{50}$ of example quaternary ammonium functionalized antimicrobial polymer 1402 (e.g., wherein "n" equals 21). An absolute $IC_{50}$ value of a chemical composition comprising doxorubicin with 0.5 $IC_{50}$ of the given example quaternary ammonium functionalized antimicrobial polymer 1402 in treating MCF7 is 0.88 μg/mL. Cytotoxicity graph 2208 regards treating MCF7 with a combination therapy of doxorubicin with 0.5 $IC_{50}$ of example guanidinium functionalized antimicrobial polymer 1404 (e.g., wherein "m" equals 20). An absolute $IC_{50}$ value of a chemical composition comprising doxorubicin with 0.5 $IC_{50}$ of the given example guanidinium functionalized antimicrobial polymer 1404 in treating MCF7 is 0.20 μg/mL. Thus, FIG. 22 demonstrates that the presence of the antimicrobial polymers can be highly advantageous at enhancing the anticancer activity of chemotherapeutic agents against therapeutic-resistance cancer cell lines (e.g., as shown in FIG. 19), as compared to therapeutic-susceptible cancer cell lines (e.g., as shown in FIG. 22).

Figure 23:
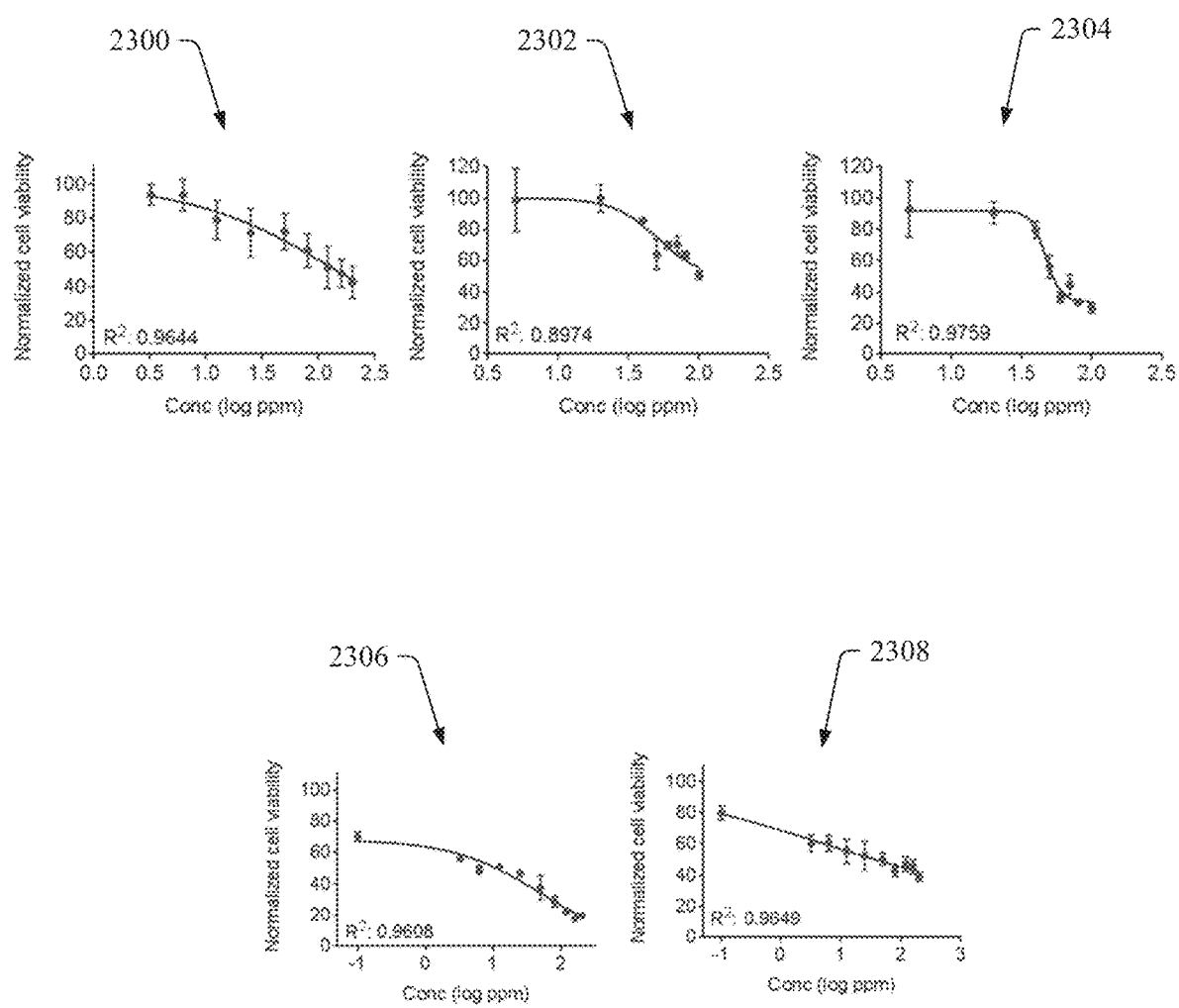
FIG. 23 illustrates diagrams of example, non-limiting graphs that can demonstrate the efficacy of anticancer activity by a chemical composition comprising one or more chemotherapeutic agents and macromolecular chemotherapeutic polycarbonate polymers in accordance with one or more embodiments described herein.

FIG. 23 illustrates a diagram of example, non-limiting cytotoxicity graphs regarding one or more combination therapies utilizing a chemical composition that combines doxorubicin with antimicrobial polymers (e.g., quaternary ammonium functionalized polycarbonate structures 102, guanidinium functionalized polycarbonate structures 104, and/or quaternary ammonium and guanidinium functionalized polycarbonate structure 106) to treat a therapeutic-resistant MCF7/ADR cell line in accordance with one or more embodiments described herein. Repetitive description of like elements employed in other embodiments described herein is omitted for sake of brevity.

Cytotoxicity graph 2300 regards treating MCF7/ADR solely with doxorubicin. An absolute $IC_{50}$ value of doxorubicin in treating MCF7/ADR is 139 µg/mL. Cytotoxicity graph 2302 regards treating MCF7/ADR solely with the example quaternary ammonium functionalized antimicrobial polymer 1402 (e.g., wherein "n" equals 21). An absolute $IC_{50}$ value of the given example quaternary ammonium functionalized antimicrobial polymer 1402 in treating MCF7/ADR is 193 µg/mL. Cytotoxicity graph 2304 regards treating MCF7/ADR solely with the example guanidinium functionalized antimicrobial polymer 1404 (e.g., wherein "m" equals 20). An absolute $IC_{50}$ value of the given example guanidinium functionalized antimicrobial polymer 1404 in treating MCF7/ADR is 53.0 µg/mL. Cytotoxicity graph 2306 regards treating MCF7/ADR with a combination therapy of doxorubicin with 0.5 $IC_{50}$ of the example quaternary ammonium functionalized antimicrobial polymer 1402 (e.g., wherein "n" equals 21). An absolute $IC_{50}$ value of a chemical composition comprising doxorubicin with 0.5 $IC_{50}$ of the given example quaternary ammonium functionalized antimicrobial polymer 1402 in treating MCF7/ADR is 11.2 µg/mL. Cytotoxicity graph 2308 regards treating MCF7/ADR with a combination therapy of doxorubicin with 0.5 $IC_{50}$ of the given example guanidinium functionalized antimicrobial polymer 1404 (e.g., wherein "m" equals 20). An absolute $IC_{50}$ value of a chemical composition comprising doxorubicin with 0.5 $IC_{50}$ of the given example guanidinium functionalized antimicrobial polymer 1404 in treating MCF7/ADR is 0.20 µg/mL. Thus, FIG. 23 demonstrates that the presence of the one or more quaternary ammonium functionalized polycarbonate structures 102 (e.g., such as example quaternary ammonium functionalized antimicrobial polymers 1402) and/or guanidinium functionalized polycarbonate structures 106 (e.g., such as guanidinium functionalized antimicrobial polymers 1404) can enhance the anticancer activity of one or more chemotherapeutic agents (e.g., doxorubicin) against therapeutic-resistant cancer cells.

Figure 24:
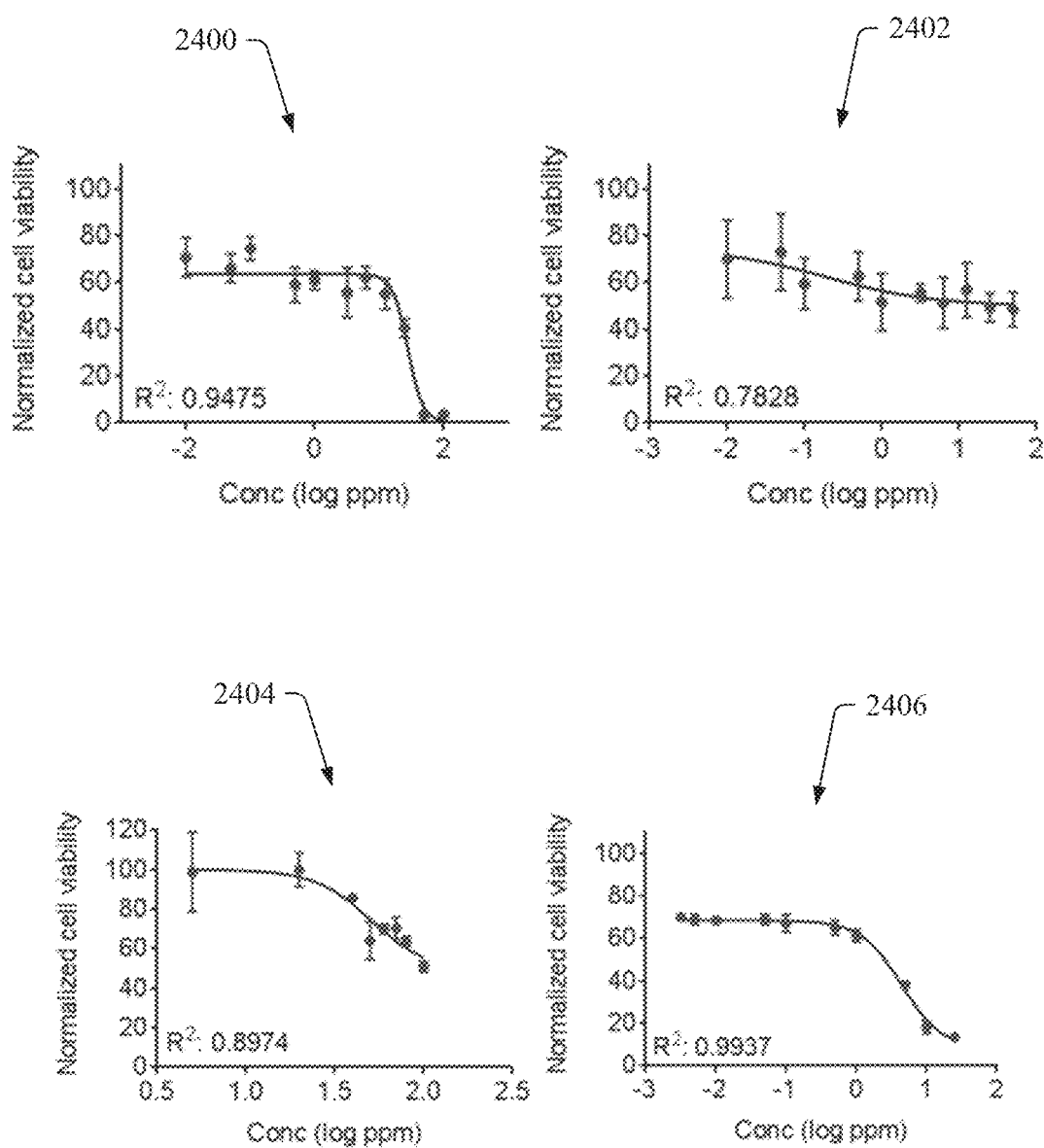
FIG. 24 illustrates diagrams of example, non-limiting graphs that can demonstrate the efficacy of anticancer activity by a chemical composition comprising one or more chemotherapeutic agents and macromolecular chemotherapeutic polycarbonate polymers in accordance with one or more embodiments described herein.

FIG. 24 illustrates a diagram of example, non-limiting cytotoxicity graphs regarding one or more combination therapies utilizing a chemical composition that combines paclitaxel with the quaternary ammonium functionalized polycarbonate structures 102 to treat therapeutic-susceptible MCF7 and/or therapeutic-resistant MCF7/ADR cell line in accordance with one or more embodiments described herein. Repetitive description of like elements employed in other embodiments described herein is omitted for sake of brevity.

Cytotoxicity graph 2400 regards treating MCF7 solely with paclitaxel. An absolute $IC_{50}$ value of paclitaxel in treating MCF7 is 19.7 µg/mL. Cytotoxicity graph 2402 regards treating MCF7/ADR solely with paclitaxel. An absolute $IC_{50}$ value of paclitaxel in treating MCF7/ADR is 5149 µg/mL. Cytotoxicity graph 2404 regards treating MCF7/ADR solely with the example quaternary ammonium functionalized antimicrobial polymer 2402 (e.g., wherein "n" equals 21). An absolute $IC_{50}$ value of the given example quaternary ammonium functionalized antimicrobial polymer 1402 in treating MCF7/ADR is 193 µg/mL. Cytotoxicity graph 2406 regards treating MCF7/ADR with a combination therapy of paclitaxel with 0.5 $IC_{50}$ of the example quaternary ammonium functionalized antimicrobial polymer 1402 (e.g., wherein "n" equals 21). An absolute $IC_{50}$ value of a chemical composition comprising paclitaxel with 0.5 $IC_{50}$ of the given example quaternary ammonium functionalized antimicrobial polymer 1402 in treating MCF7/ADR is 2.53 µg/mL. Thus, FIG. 24 demonstrates that the presence of the one or more quaternary ammonium functionalized polycarbonate structures 102 (e.g., such as the example quaternary ammonium functionalized antimicrobial polymers 1402) can enhance the anticancer activity of one or more chemotherapeutic agents (e.g., paclitaxel) against therapeutic-resistant cancer cells.

Figure 25:
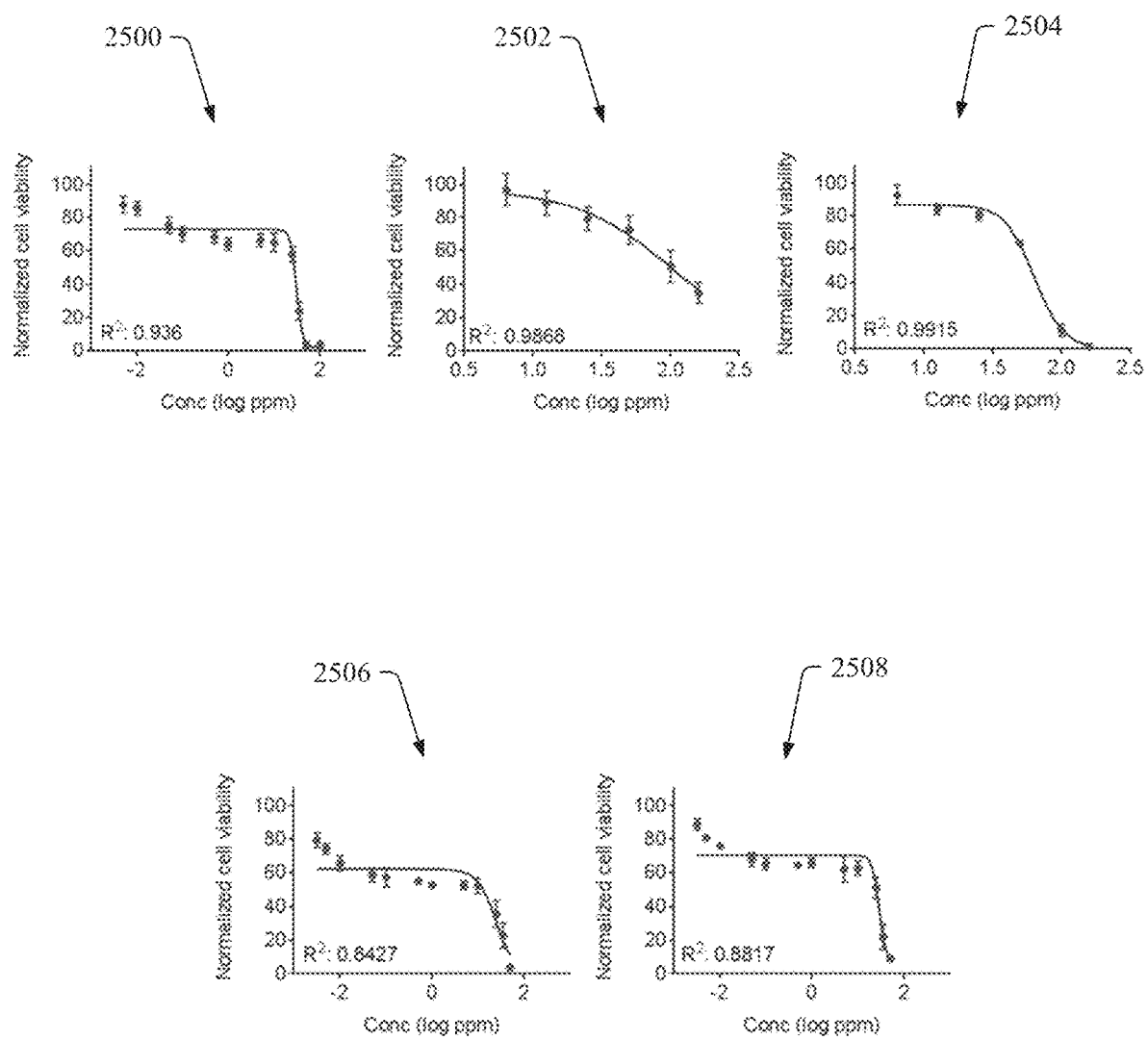
FIG. 25 illustrates diagrams of example, non-limiting graphs that can demonstrate the efficacy of anticancer activity by a chemical composition comprising one or more chemotherapeutic agents and macromolecular chemotherapeutic polycarbonate polymers in accordance with one or more embodiments described herein.

FIG. 25 illustrates a diagram of example, non-limiting cytotoxicity graphs regarding one or more combination therapies utilizing a chemical composition that combines paclitaxel with antimicrobial polymers (e.g., quaternary ammonium functionalized polycarbonate structures 102, guanidinium functionalized polycarbonate structures 104, and/or quaternary ammonium and guanidinium functionalized polycarbonate structure 106) to treat a therapeutic-resistant SK-OV-3-TR cell line in accordance with one or more embodiments described herein. Repetitive description of like elements employed in other embodiments described herein is omitted for sake of brevity.

Cytotoxicity graph 2500 regards treating SK-OV-3-TR solely with paclitaxel. An absolute $IC_{50}$ value of paclitaxel in treating SK-OV-3 is 27.4 µg/mL. Cytotoxicity graph 2502 regards treating SK-OV-3-TR solely with the example quaternary ammonium functionalized antimicrobial polymer 1402 (e.g., wherein "n" equals 21). An absolute $IC_{50}$ value of the given example quaternary ammonium functionalized antimicrobial polymer 1402 in treating SK-OV-3-TR is 100 µg/mL. Cytotoxicity graph 2504 regards treating SK-OV-3-TR solely with the example guanidinium functionalized antimicrobial polymer 1404 (e.g., wherein "m" equals 20). An absolute $IC_{50}$ value of the given example guanidinium functionalized antimicrobial polymer 1404 in treating SK-OV-3-TR is 58.8 µg/mL. Cytotoxicity graph 2506 regards treating SK-OV-3-TR with a combination therapy of paclitaxel with 0.5 $IC_{50}$ of the example quaternary ammonium functionalized antimicrobial polymer 1402 (e.g., wherein "n" equals 21). An absolute $IC_{50}$ value of a chemical composition comprising paclitaxel with 0.5 $IC_{50}$ of the given example quaternary ammonium functionalized antimicrobial polymer 1402 in treating SK-OV-3-TR is 13.0 µg/mL. Cytotoxicity graph 2508 regards treating SK-OV-3-TR with a combination therapy of paclitaxel with 0.5 $IC_{50}$ of example guanidinium functionalized antimicrobial polymer 1404 (e.g., wherein "m" equals 20). An absolute $IC_{50}$ value of a chemical composition comprising paclitaxel with 0.5 $IC_{50}$ of the given guanidinium functionalized antimicrobial polymer 1404 in treating SK-OV-3-TR is 25.2 µg/mL. Thus, FIG. 25 demonstrates that the presence of the antimicrobial polymers can advantageously enhance the anticancer activity of chemotherapeutic agents (e.g., paclitaxel) against therapeutic-resistance cancer cell lines, such as SK-OV-3-TR.

FIG. 26 illustrates a flow diagram of an example, non-limiting method 2600 that can facilitate utilizing one or more combination therapies comprising chemotherapeutic agents and antimicrobial polymers to treat cancer cells in accordance with one or more embodiments described herein. Repetitive description of like elements employed in other embodiments described herein is omitted for sake of brevity.

At 2602, the method 2600 can comprise inhibiting a growth of cancer cells (e.g., therapeutic-susceptible or therapeutic-resistant cancer cells) by administering a combination therapy that includes one or more chemotherapeutic agents and antimicrobial polymers (e.g., characterized by the one or more quaternary ammonium functionalized polycarbonate structures 102, guanidinium functionalized polycarbonate structures 104, and/or quaternary ammonium and guanidinium functionalized polycarbonate structure 106). Example chemotherapeutic agents that can be included in the combination therapy can include, but are not limited to: doxorubicin, paclitaxel, a combination thereof, and/or the like. Additionally, the example quaternary ammonium functionalized antimicrobial polymers 1402, example guanidinium functionalized antimicrobial polymers 1404, and/or quaternary ammonium and guanidinium functionalized antimicrobial polymers 1406 can exemplify the one or more antimicrobial polymers.

At 2604, the method 2600 can comprise enhancing an anticancer activity of the one or more chemotherapeutic agents by the presence of the one or more antimicrobial polymers. For example, the one or more antimicrobial polymers can exhibit a lytic mechanism and/or translocation mechanism that can enhance the anticancer activity of the one or more chemotherapeutic agents. For instance, one or more quaternary ammonium functionalized polycarbonate structures 102 (e.g., such as example quaternary ammonium functionalized antimicrobial polymers 1402) can exhibit a lytic mechanism against the cancer cells. In another instance, one or more guanidinium functionalized polycarbonate structures 104 (e.g., such as example guanidinium functionalized antimicrobial polymers 1404) can exhibit a translocation mechanism against the cancer cells. In a further instance, one or more quaternary ammonium and guanidinium functionalized polycarbonate structures 106 (e.g., such as example quaternary ammonium and guanidinium functionalized antimicrobial polymers 1406) can exhibit a lytic and/or translocation mechanism against the cancer cells. In various embodiments, the lytic and/or translocation mechanisms of the antimicrobial polymers can have a synergistic effect with the anticancer activity of the one or more chemotherapeutic agents.

Figure 27:
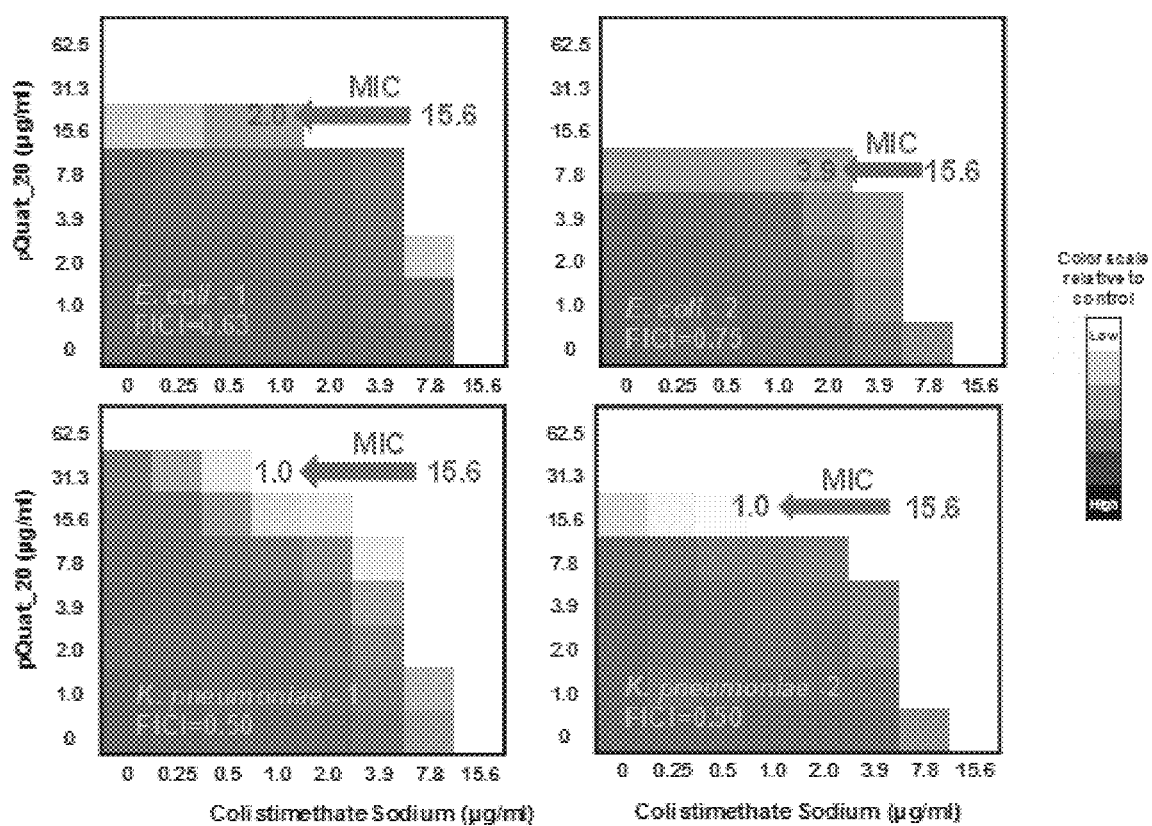
FIG. 27 illustrate diagrams of example, non-limiting checkerboard assays that can depict the efficacy of antimicrobial activity exhibited by a chemical composition comprising an antimicrobial agent and one or more antimicrobial polymers in accordance with one or more embodiments described herein.

FIG. 27 illustrates a diagram of example, non-limiting checkerboard assays that can demonstrate the enhanced antimicrobial activity of one or more combination therapies comprising an antimicrobial agent and the one or more antimicrobial polymers described herein (e.g., characterized by the quaternary ammonium functionalized polycarbonate structures 102, guanidinium functionalized polycarbonate structures 104, and/or quaternary ammonium and guanidinium ammonium functionalized polycarbonate structures 106). Repetitive description of like elements employed in other embodiments described herein is omitted for sake of brevity.

Plasmid-mediated colistin-resistance has been reported in Gram-negative bacteria, which resulted from a MCR-1 enzyme that catalyzes the transfer of phosphoethanolamine to lipid A; thereby rendering the membrane more electropositive. The MIC of colistimethate sodium against two MCR-1-positive E. coli strains was determined to be 15.6 and 31.3 µg/mL, respectively, higher than the breakpoints for susceptibility testing (e.g., 4-8 µg/mL for Gram-negative bacteria). However, the example quaternary ammonium functionalized antimicrobial polymer (e.g., wherein "n" is 20) ("pQuat_20") at ½×MIC can significantly lower colistin MIC to <0.49 µg/mL (e.g., about 31 to 63 fold reductions), sensitizing the MCR-1 colistin-resistant bacteria to colistin treatment.

As shown in FIG. 27, pQuat_20/colistimethate sodium can have an additive effect against the colistin-resistant E. coli strains. A synergistic effect can also be seen between pQuat_20 and colistimethate sodium against K. pneumoniae strains. The presence of quaternary ammonium functionalized polycarbonate structures 102 (e.g., such as example quaternary ammonium functionalized antimicrobial polymer 1402) can reverse colistimethate sodium resistance phenotype, decreasing MIC.

Figure 28:
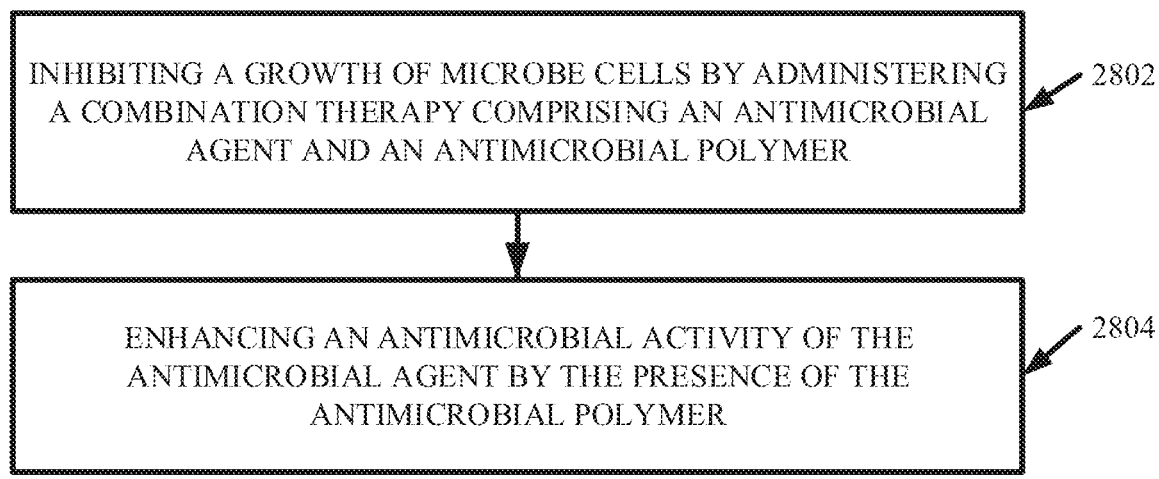
FIG. 28 illustrates a flow diagram of an example, non-limiting method that can facilitate performing a combination therapy utilizing one or more antimicrobial agents and antimicrobial polymers to inhibit the growth of microbe cells (e.g., bacteria and/or fungi cells) in accordance with one or more embodiments described herein.

FIG. 28 illustrates a flow diagram of an example, non-limiting method 2800 that can facilitate utilizing one or more combination therapies comprising antimicrobial agents and antimicrobial polymers to treat cancer cells in accordance with one or more embodiments described herein. Repetitive description of like elements employed in other embodiments described herein is omitted for sake of brevity.

At 2802, the method 2800 can comprise inhibiting a growth of microbe cells (e.g., therapeutic-susceptible or therapeutic-resistant microbe cells, including various bacteria and/or fungus cells) by administering a combination therapy that includes one or more antimicrobial agents and antimicrobial polymers (e.g., characterized by the one or more quaternary ammonium functionalized polycarbonate structures 102, guanidinium functionalized polycarbonate structures 104, and/or quaternary ammonium and guanidinium functionalized polycarbonate structure 106). Example antimicrobial agents that can be included in the combination therapy can include, but are not limited to: colistin, antimicrobial peptides (e.g., defensins), a combination thereof, and/or the like. Additionally, the example quaternary ammonium functionalized antimicrobial polymers 1402, example guanidinium functionalized antimicrobial polymers 1404, and/or quaternary ammonium and guanidinium functionalized antimicrobial polymers 1406 can exemplify the one or more antimicrobial polymers.

At 2804, the method 2800 can comprise enhancing an antimicrobial activity of the one or more antimicrobial agents by the presence of the one or more antimicrobial polymers. For example, the one or more antimicrobial polymers can exhibit a lytic mechanism and/or translocation mechanism that can enhance the antimicrobial activity of the one or more antimicrobial agents. For instance, one or more quaternary ammonium functionalized polycarbonate structures 102 (e.g., such as example quaternary ammonium functionalized antimicrobial polymers 1402) can exhibit a lytic mechanism against the microbe cells. In another instance, one or more guanidinium functionalized polycarbonate structures 104 (e.g., such as example guanidinium functionalized antimicrobial polymers 1404) can exhibit a translocation mechanism against the microbe cells. In a further instance, one or more quaternary ammonium and guanidinium functionalized polycarbonate structures 106 (e.g., such as example quaternary ammonium and guanidinium functionalized antimicrobial polymers 1406) can exhibit a lytic and/or translocation mechanism against the microbe cells. In various embodiments, the lytic and/or translocation mechanisms of the antimicrobial polymers can have a synergistic effect with the antimicrobial activity of the one or more antimicrobial agents.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

It is, of course, not possible to describe every conceivable combination of components, products and/or methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A chemical composition, comprising:

a first triblock polymer comprising a quaternary ammonium functionalized polycarbonate block and exhibiting anticancer activity via a lytic mechanism; and a second triblock polymer comprising a guanidinium functionalized polycarbonate block and exhibiting anticancer activity via a translocation mechanism, wherein the first triblock polymer and the second triblock polymer form a stereocomplex providing kinetic stability, wherein the first triblock polymer has a structure selected from the group consisting of

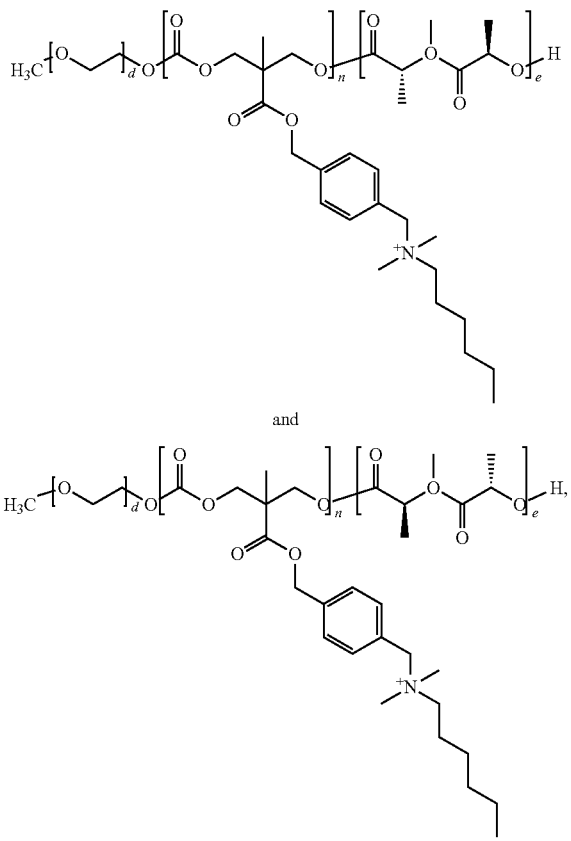

and wherein "d" is a first integer that is greater than or equal to 45 and less than or equal to 450, wherein "n" is a second integer that is greater than or equal to 5 and less than or equal to 75, and wherein "e" is a third integer that is greater than or equal to 7 and less than or equal to 100.

2. The chemical composition of claim 1, wherein the stereocomplex characterized by a size greater than or equal to 1 nanometer and less than or equal to 100 nanometers.

3. The chemical composition of claim 1, wherein the first triblock polymer and the second triblock polymer are cationic and biodegradable.

4. The chemical composition of claim 1, wherein the second triblock polymer has a structure selected from the group consisting of

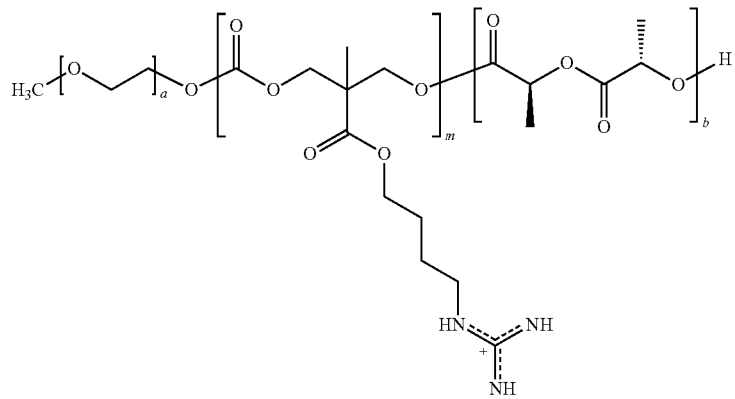

and

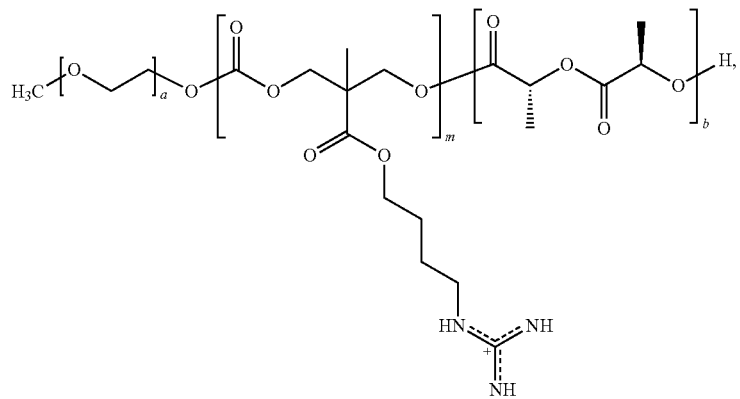

wherein a is "a" first integer that is greater than or equal to 45 and less than or equal to 450, wherein "m" is a second integer that is greater than or equal to 5 and less than or equal to 75, and wherein "b" is a third integer that is greater than or equal to 7 and less than or equal to 100.

5. The chemical composition of claim 1, wherein the translocation mechanism comprises translocating the second triblock polymer across a cell membrane and binding a cytosolic member.

6. The chemical composition of claim 5, wherein the cytosolic member is selected from the group consisting of a protein, an enzyme, and a gene.

7. The chemical composition of claim 1, wherein the first triblock polymer has a first polylactic acid block, and wherein the second triblock polymer has a second polylactic acid block.

8. A chemical composition, comprising:
a quaternary ammonium functionalized polycarbonate polymer that exhibits antimicrobial activity via a lytic mechanism; and
a guanidinium functionalized polycarbonate polymer that exhibits antimicrobial activity via a translocation mechanism, wherein the quaternary ammonium functionalized polycarbonate polymer and the guanidinium functionalized polycarbonate polymer form a stereocomplex providing kinetic stability,
wherein the quaternary ammonium functionalized polycarbonate polymer has a structure selected from the group consisting of

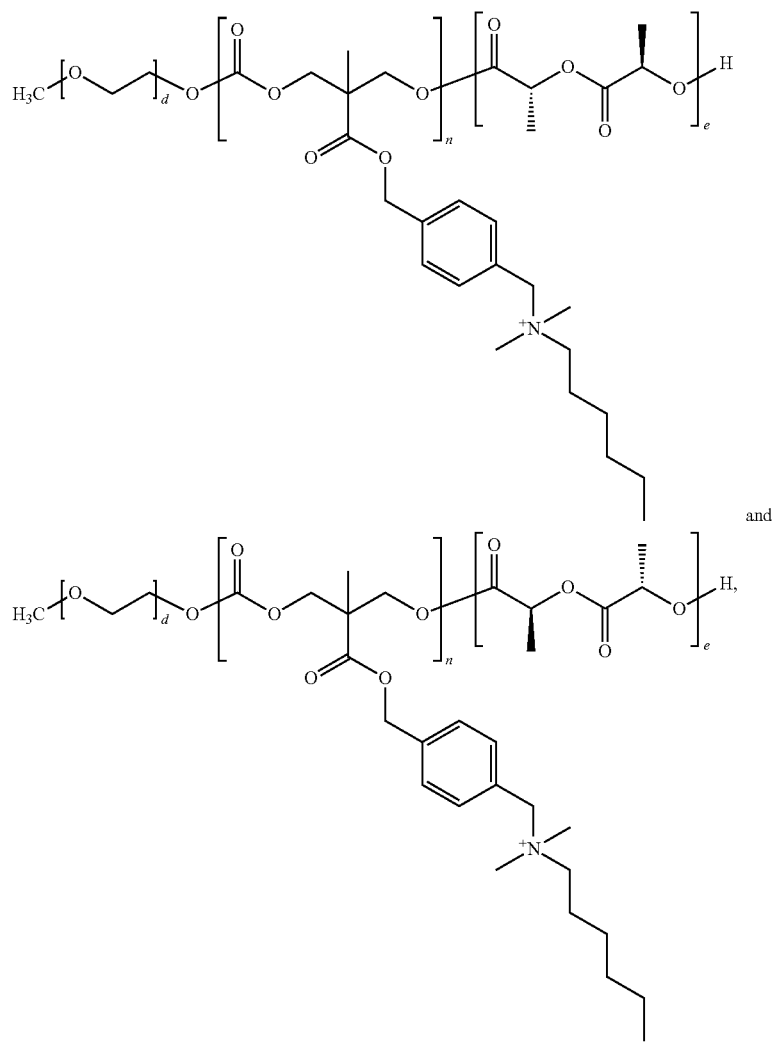

and wherein "d" is a first integer that is greater than or equal to 45 and less than or equal to 450, wherein "n" is a second integer that is greater than or equal to 5 and less than or equal to 75, and wherein "e" is a third integer that is greater than or equal to 7 and less than or equal to 100.

9. The chemical composition of claim 8, wherein the quaternary ammonium functionalized polycarbonate polymer and the guanidinium functionalized polycarbonate polymer are cationic and biodegradable.

10. The chemical composition of claim 8, wherein the translocation mechanism comprises translocating the guanidinium functionalized polycarbonate polymer across a cell membrane and binding a cytosolic member.

11. The chemical composition of claim 10, wherein the cytosolic member is selected from the group consisting of a protein, an enzyme, and a gene.

* * * * *